United States Patent
Ovalles et al.

(10) Patent No.: US 9,921,205 B2
(45) Date of Patent: Mar. 20, 2018

(54) METHOD FOR DETERMINING THE EFFECTIVENESS OF ASPHALTENE DISPERSANT ADDITIVES FOR INHIBITING OR PREVENTING ASPHALTENE PRECIPITATION IN A HYDROCARBON-CONTAINING MATERIAL SUBJECTED TO ELEVATED TEMPERATURE AND PRESSSURE CONDITIONS

(71) Applicants: Cesar Ovalles, Walnut Creek, CA (US); Estrella Rogel, Orinda, CA (US); Michael Moir, San Rafael, CA (US)

(72) Inventors: Cesar Ovalles, Walnut Creek, CA (US); Estrella Rogel, Orinda, CA (US); Michael Moir, San Rafael, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 714 days.

(21) Appl. No.: 13/675,065

(22) Filed: Nov. 13, 2012

(65) Prior Publication Data
US 2014/0130581 A1    May 15, 2014

(51) Int. Cl.
| | | |
|---|---|---|
| *G01N 33/28* | (2006.01) | |
| *C10G 29/02* | (2006.01) | |
| *C09K 8/04* | (2006.01) | |
| *C09K 8/50* | (2006.01) | |
| *C09K 8/57* | (2006.01) | |
| *C09K 8/62* | (2006.01) | |

(52) U.S. Cl.
CPC ........... *G01N 33/2835* (2013.01); *C09K 8/04* (2013.01); *C09K 8/50* (2013.01); *C09K 8/57* (2013.01); *C09K 8/62* (2013.01); *C10G 29/02* (2013.01); *G01N 33/2823* (2013.01)

(58) Field of Classification Search
CPC ....................................................... G01N 33/28
USPC ....................................................... 73/61.55
See application file for complete search history.

(56) References Cited

U.S. PATENT DOCUMENTS

| | | |
|---|---|---|
| 4,634,680 A | 1/1987 | Kingsley |
| 5,143,594 A | 9/1992 | Stephenson et al. |
| 6,773,921 B1 | 8/2004 | Schabron et al. |

(Continued)

FOREIGN PATENT DOCUMENTS

| | | |
|---|---|---|
| CA | 2326288 | 5/2001 |
| DE | 19709797 A1 | 9/1998 |

(Continued)

OTHER PUBLICATIONS

Al-Sahhaf, Taher et al., Retardation of asphaltene precipitation by addition of toluene resins, deasphalted oil and surfactants, Fluid Phase Equilibria 194-197 (2002), pp. 1045-1057.*

(Continued)

*Primary Examiner* — Peter Macchiarolo
*Assistant Examiner* — Alexander Mercado
(74) *Attorney, Agent, or Firm* — Ryan, Mason & Lewis, LLP

(57) ABSTRACT

Disclosed herein is a method for determining the effectiveness of one or more asphaltene dispersant additives for inhibiting or preventing asphaltene precipitation in a hydrocarbon-containing material subjected to elevated temperature and pressure conditions.

15 Claims, 5 Drawing Sheets

(56) References Cited

U.S. PATENT DOCUMENTS

| | | | |
|---|---|---|---|
| 8,236,564 | B2 | 8/2012 | Pauli et al. |
| 8,241,920 | B2 | 8/2012 | Schabron et al. |
| 8,273,581 | B2 | 9/2012 | Schabron et al. |
| 8,367,425 | B1 | 2/2013 | Schabron et al. |
| 8,492,154 | B1 † | 7/2013 | Schabron |
| 8,530,240 | B1 | 9/2013 | Schabron et al. |
| 8,628,970 | B1 | 1/2014 | Schabron et al. |
| 9,353,317 | B2 | 5/2016 | Schabron et al. |
| 9,458,389 | B1 | 10/2016 | Schabron et al. |
| 2004/0039125 | A1 | 2/2004 | Breuer et al. |
| 2004/0050752 | A1 | 3/2004 | Leinweber et al. |
| 2004/0163995 | A1 | 8/2004 | Cornelisse |
| 2004/0232042 | A1 | 11/2004 | Mukkamala |
| 2004/0232043 | A1 | 11/2004 | Mukkamala |
| 2004/0232044 | A1 | 11/2004 | Mukkamala |
| 2004/0238404 | A1 | 12/2004 | Mukkamala |
| 2005/0082231 | A1 | 4/2005 | Gochin |
| 2005/0091915 | A1 | 5/2005 | Behler |
| 2006/0079434 | A1 | 4/2006 | Banavali et al. |
| 2006/0096757 | A1 | 5/2006 | Berry et al. |
| 2006/0096758 | A1 | 5/2006 | Berry et al. |
| 2007/0048874 | A1 * | 3/2007 | Schabron et al. ............ 436/141 |
| 2010/0251935 | A1 | 10/2010 | Pauli et al. |
| 2012/0160015 | A1 | 6/2012 | Ovalles et al. |
| 2014/0021101 | A1 † | 1/2014 | Schabron |

FOREIGN PATENT DOCUMENTS

| | | |
|---|---|---|
| EP | 1091085 | 4/2001 |
| WO | 8801180 | 2/1988 |
| WO | 9314147 A1 | 1/1993 |
| WO | 9719987 | 6/1997 |
| WO | 9916810 | 4/1999 |
| WO | 0056804 | 9/2000 |
| WO | 0058388 | 10/2000 |
| WO | 200174966 A1 | 10/2001 |
| WO | 2004033602 A1 | 4/2004 |
| WO | 2005010126 A1 | 2/2005 |
| WO | 2005054321 A1 | 6/2005 |
| WO | 2006047745 A1 | 5/2006 |

OTHER PUBLICATIONS

Fan, et al. (2010) "Investigation of Fouling Mechanisms of a Light Crude Oil Using an Alcor Hot Liquid Process Simulator", Energy & Fuels, pp. 6110-6118.

Watkinson et al. (2000) "Fouling of a Sweet Crude Oil Under Inert and Oxygenated Conditions", Energy & Fuels, pp. 64-69.

Dickakian, et al. (1988) "Asphaltene Precipitation Primary Crude Exchanger Fouling Mechanism", Technology pp. 47-50.

Watkinson (2003) "Heat of Crude Oil Fouling Using Two Different Probes", ECI Digital Archives, pp. 1-7.

Garcia (2001) "Asphaltenes Deposition Control in Lake Maracaibo Crude Oil Production", SPE International Symposium, pp. 1-9.

M.M. Boduszynski et al., "Separation of Solvent-Refined Coal into Solvent-Derived Fractions," Analytical Chemistry, 1982, pp. 372-375, vol. 54, No. 3.

F.P. Burke et al., "Liquid Column Fractionation: A Method of Solvent Fractionation of Coal Liquefaction and Petroleum Products," Fuel, 1979, pp, 539-541, vol. 28, No. 7.

F.K. Schweighardt et al., "Evaluation of Analytical Techniques for SRC-1 Characterization, Recycle Solvent Studies, and Product Fractionation Studies: Development of SRC-1 Product Analysis," United States Department of Energy Technical Report No. DOE/OR/03054-61—vol. 2, Sep. 1983, pp. 250 and 276.

Al-Sahhaf, Taher A. et al. Retardation of asphaltene precipitation by addition of toluene, resins, deasphalted oil and surfactants. Fluid Phase Equilibria 194-197 (2002) 1045-1057.†

Xiang, Yanqiao et al. Ultrahigh pressure liquid chromatography using elevated temperature. Journal of Chromatography A, 1104 (2006) 198-202.†

U.S. Appl. No. 60/711,599. Date of publication Jul. 23, 2013.†

Xiang, Yanqiao et al, Ultrahigh pressure liquid chromatography using elevated temperature. Journal of Chromatography A, 1104 (2006) 198-202.†

U.S. Appl. No. 60/711,599; date of publication Jul. 23, 2013.†

Al-Sahhaf, Taher. Retardation of asphaltene precipitation by addition of toluene resins, deasphalted oil and surfactants. Fluid Phase Equilibria 194-197 (200) 1045-1057.†

\* cited by examiner
† cited by third party

METHOD FOR DETERMINING THE EFFECTIVENESS OF ASPHALTENE DISPERSANT ADDITIVES FOR INHIBITING OR PREVENTING ASPHALTENE PRECIPITATION IN A HYDROCARBON-CONTAINING MATERIAL SUBJECTED TO ELEVATED TEMPERATURE AND PRESSSURE CONDITIONS

BACKGROUND OF THE INVENTION

1. Technical Field

The present invention generally relates to methods for determining the effectiveness of asphaltene dispersant additives for inhibiting or preventing asphaltene precipitation in a hydrocarbon-containing material subjected to elevated temperature and pressure conditions.

2. Description of the Related Art

Hydrocarbon-containing feedstocks generally contain polar core materials, such as asphaltenes, dispersed in lower polarity solvent(s). Intermediate polarity material(s), usually referred to as resin(s), can associate with the polar core materials to maintain a homogeneous mixture of the components.

The large reserves of heavy or extra heavy crude oil are very viscous in their natural state. The viscous nature of the crude oil, however, makes it difficult to transport the oil in conventional pipelines to stations where it can be processed into useful end products. The origin of high viscosity in these oils has been attributed to high asphaltene content of the oils. Asphaltenes are organic heterocyclic macromolecules which occur in crude oils. Under normal reservoir conditions, asphaltenes are usually stabilized in the crude oil by maltenes and resins that are chemically compatible with asphaltenes, but that have lower molecular weight. Polar regions of the maltenes and resins surround the asphaltene while non-polar regions are attracted to the oil phase. Thus, these molecules act as surfactants and result in stabilizing the asphaltenes in the crude. However, changes in pressure, temperature or concentration of the crude oils can alter the stability of the dispersion and increase the tendency of the asphaltenes to agglomerate into larger particles. As these asphaltene agglomerates grow, so does their tendency to precipitate out of solution. Generally, unwanted asphaltene precipitation is a concern in upstream applications due to, for example, plugging of an oil well or pipeline as well as stopping or decreasing oil production.

In downstream applications, asphaltenes are believed to be the source of coke during thermal upgrading processes thereby reducing and limiting yield of residue conversion. Presently, the petroleum industry relies more heavily on relatively high boiling feedstocks derived from materials such as coal, tar sands, oil-shale, and heavy crudes. These feedstocks generally contain significantly more undesirable components, especially from an environmental point of view. Consequently, such feedstocks and product streams require more severe upgrading in order to reduce the content of such undesirable components. More severe upgrading, of course, adds considerably to the expense of processing these petroleum streams.

As discussed above, asphaltenes are believed to be the source of coke during thermal upgrading processes thereby reducing and limiting yield of residue conversion. In catalytic upgrading processes, asphaltenes can contribute to catalyst poisoning by coke and metal deposition thereby limiting the activity of the catalyst. Asphaltenes can also cause fouling in, for example, heat exchangers and other equipment in a refinery. Fouling in heat transfer equipments used for streams of petroleum origin can result from a number of mechanisms including chemical reactions, corrosion and the deposit of materials made insoluble by the temperature difference between the fluid and heat exchange wall. The presence of insoluble contaminants may exacerbate the problem: blends of a low-sulfur, low asphaltene (LSLA) crude oil and a high-sulfur, high asphaltene (HSHA) crude, for example, may be subject to a significant increase in fouling in the presence of iron oxide (rust) particulates. Subsequent exposure of the precipitated asphaltenes over time to the high temperatures then causes formation of coke as a result of thermal degradation.

The precipitation of asphaltenes can be prevented or reduced by small amounts of dispersants. These dispersants display one or more of the following effects:

a) the amount of precipitate is reduced;
    b) the precipitate is formed more slowly;
    c) the precipitate is more finely divided; and
    d) the tendency of the precipitate to deposit on surfaces is reduced.

Accordingly, it would be advantageous to characterize a hydrocarbon-containing material such as a hydrocarbon-containing feedstock which has been subjected to elevated temperature and pressure conditions, i.e., reservoir or process conditions, in order to minimize problems associated with asphaltene precipitation in upstream and downstream applications. Thus, it would be desirable to provide improved methods for determining the effectiveness of one or more asphaltene dispersant additives for inhibiting or preventing asphaltene precipitation in a hydrocarbon-containing material subjected to elevated temperature and pressure conditions.

SUMMARY OF THE INVENTION

In accordance with one embodiment of the present invention, there is provided a method for determining effectiveness of one or more asphaltene dispersant additives for inhibiting or preventing asphaltene precipitation in a hydrocarbon-containing material subjected to elevated temperature and pressure conditions, the method comprising the steps of:

(a) subjecting a first column having an inert packing material therein to a first set of elevated temperature and pressure conditions;

(b) precipitating an amount of asphaltenes from a first hydrocarbon-containing material sample having solvated asphaltenes therein with one or more first asphaltene-precipitating mobile phase solvents and capturing the precipitated asphaltenes in the inert packing material in the first column;

(c) dissolving an amount of the precipitated asphaltenes at a predetermined temperature with one or more second solvents having a solubility parameter of at least about 21 $MPa^{0.5}$ but no greater than about 30 $MPa^{0.5}$ to elute a fraction having dissolved asphaltenes therein;

(d) determining the asphaltene content of the first sample by the concentration of asphaltenes in the eluted fraction from the first column;

(e) subjecting the first column or a second column having an inert packing material therein to a second set of elevated temperature and pressure conditions;

(f) precipitating an amount of asphaltenes from a second hydrocarbon-containing material sample containing one or more asphaltene dispersant additives and having solvated asphaltenes therein with one or more second asphaltene-precipitating mobile phase solvents and capturing the precipitated asphaltenes in the inert packing material in the second column;

(g) dissolving an amount of the precipitated asphaltenes at predetermined temperature with one or more second solvents having a solubility parameter of at least about 21 MPa$^{0.5}$ but no greater than about 30 MPa$^{0.5}$ to elute a fraction having dissolved asphaltenes therein;

(h) determining the asphaltene content of the second sample by the concentration of asphaltenes in the eluted fraction from the second column; and (i) comparing the asphaltene content of the first sample with the asphaltene content of the second sample.

In accordance with a second embodiment of the present invention, there is provided a method for reducing fouling in one or more crude hydrocarbon refinery components located within a refinery, the method comprising the steps of:

(a) selecting one or more asphaltene dispersant additives for adding to one or more hydrocarbon-containing feedstocks to be refined, wherein the selection of the one or more asphaltene dispersant additives comprises receiving data corresponding to the effectiveness of the one or more asphaltene dispersant additives for inhibiting or preventing asphaltene precipitation in a hydrocarbon-containing feedstock subjected to elevated temperature and pressure conditions; wherein the data is derived from:

(i) subjecting a first column having an inert packing material therein to a first set of elevated temperature and pressure conditions;

(ii) precipitating an amount of asphaltenes from a first hydrocarbon-containing feedstock sample having solvated asphaltenes therein with one or more first asphaltene-precipitating mobile phase solvents and capturing the precipitated asphaltenes in the inert packing material in the first column;

(iii) dissolving an amount of the precipitated asphaltenes at predetermined temperature with one or more second solvents having a solubility parameter of at least about 21 MPa$^{0.5}$ but no greater than about 30 MPa$^{0.5}$ to elute a fraction having dissolved asphaltenes therein;

(iv) determining the asphaltene content of the first sample by the concentration of asphaltenes in the eluted fraction from the first column;

(v) subjecting the first column or a second column having an inert packing material therein to a second set of elevated temperature and pressure conditions;

(vi) precipitating an amount of asphaltenes from a second hydrocarbon-containing feedstock sample containing one or more asphaltene dispersant additives and having solvated asphaltenes therein with one or more second asphaltene-precipitating mobile phase solvents and capturing the precipitated asphaltenes in the inert packing material in the second column;

(vii) dissolving an amount of the precipitated asphaltenes at predetermined temperature with one or more second solvents having a solubility parameter of at least about 21 MPa$^{0.5}$ but no greater than about 30 MPa$^{0.5}$ to elute a fraction having dissolved asphaltenes therein;

(viii) determining the asphaltene content of the second sample by the concentration of asphaltenes in the eluted fraction from the second column; and (ix) comparing the asphaltene content of the first sample with the asphaltene content of the second sample.

(b) adding an effective amount of the selected one or more asphaltene dispersant additives to the one or more hydrocarbon-containing feedstocks to be refined; and (c) feeding the one or more hydrocarbon-containing feedstocks to the one or more crude hydrocarbon refinery components.

In accordance with a third embodiment of the present invention, there is provided a system capable of experiencing fouling conditions associated with particulate or asphaltene fouling, the system comprising:

(a) one or more crude hydrocarbon refinery components; and (b) one or more hydrocarbon-containing feedstocks containing one or more asphaltene dispersant additives therein for providing a hydrocarbon-containing feedstock having a stable plurality of asphaltene components, wherein the one or more hydrocarbon-containing feedstocks are in fluid communication with the one or more crude hydrocarbon refinery components, and further wherein selection of the one or more asphaltene dispersant additives comprises receiving data corresponding to the effectiveness of the one or more asphaltene dispersant additives for inhibiting or preventing asphaltene precipitation in a hydrocarbon-containing feedstock subjected to elevated temperature and pressure conditions; wherein the data is derived from:

(i) subjecting a first column having an inert packing material therein to a first set of elevated temperature and pressure conditions;

(ii) precipitating an amount of asphaltenes from a first hydrocarbon-containing feedstock sample having solvated asphaltenes therein with one or more first asphaltene-precipitating mobile phase solvents and capturing the precipitated asphaltenes in the inert packing material in the first column;

(iii) dissolving an amount of the precipitated asphaltenes at predetermined temperature with one or more second solvents having a solubility parameter of at least about 21 MPa$^{0.5}$ but no greater than about 30 MPa$^{0.5}$ to elute a fraction having dissolved asphaltenes therein;

(iv) determining the asphaltene content of the first sample by the concentration of asphaltenes in the eluted fraction from the first column;

(v) subjecting the first column or a second column having an inert packing material therein to a second set of elevated temperature and pressure conditions;

(vi) precipitating an amount of asphaltenes from a second hydrocarbon-containing feedstock sample containing one or more asphaltene dispersant additives and having solvated asphaltenes therein with one or more second asphaltene-precipitating mobile phase solvents and capturing the precipitated asphaltenes in the inert packing material in the second column;

(vii) dissolving an amount of the precipitated asphaltenes at predetermined temperature with one or more second solvents having a solubility parameter of at least about 21 MPa$^{0.5}$ but no greater than about 30 MPa$^{0.5}$ to elute a fraction having dissolved asphaltenes therein;

(viii) determining the asphaltene content of the second sample by the concentration of asphaltenes in the eluted fraction from the second column; and (ix) comparing the asphaltene content of the first sample with the asphaltene content of the second sample.

In accordance with a fourth embodiment of the present invention, there is provided a method for improving flow of a hydrocarbon-containing feedstock from a well, wellhead or a production line proximate the wellhead, the method comprising the steps of:

(a) selecting one or more asphaltene dispersant additives for adding to the hydrocarbon-containing feedstock, wherein the selection of the one or more asphaltene dispersant additives comprises receiving data corresponding to the effectiveness of the one or more asphaltene dispersant additives for inhibiting or preventing asphaltene precipitation in a hydrocarbon-containing feedstock subjected to elevated temperature and pressure conditions; wherein the data is derived from:
- (i) subjecting a first column having an inert packing material therein to a first set of elevated temperature and pressure conditions;
- (ii) precipitating an amount of asphaltenes from a first hydrocarbon-containing feedstock sample having solvated asphaltenes therein with one or more first asphaltene-precipitating mobile phase solvents and capturing the precipitated asphaltenes in the inert packing material in the first column;
- (iii) dissolving an amount of the precipitated asphaltenes at predetermined temperature with one or more second solvents having a solubility parameter of at least about 21 $MPa^{0.5}$ but no greater than about 30 $MPa^{0.5}$ to elute a fraction having dissolved asphaltenes therein;
- (iv) determining the asphaltene content of the first sample by the concentration of asphaltenes in the eluted fraction from the first column;
- (v) subjecting the first column or a second column having an inert packing material therein to a second set of elevated temperature and pressure conditions;
- (vi) precipitating an amount of asphaltenes from a second hydrocarbon-containing feedstock sample containing one or more asphaltene dispersant additives and having solvated asphaltenes therein with one or more second asphaltene-precipitating mobile phase solvents and capturing the precipitated asphaltenes in the inert packing material in the second column;
- (vii) dissolving an amount of the precipitated asphaltenes at predetermined temperature with one or more second solvents having a solubility parameter of at least about 21 $MPa^{0.5}$ but no greater than about 30 $MPa^{0.5}$ to elute a fraction having dissolved asphaltenes therein;
- (viii) determining the asphaltene content of the second sample by the concentration of asphaltenes in the eluted fraction from the second column; and
- (ix) comparing the asphaltene content of the first sample with the asphaltene content of the second sample; and
- (b) injecting the selected one or more asphaltene dispersant additives into the well, wellhead or a production line proximate the wellhead.

In accordance with a fifth embodiment of the present invention, there is provided a method for optimizing the concentration of asphaltene dispersant additives in a hydrocarbon-containing material, the method comprising the steps of:
- (a) selecting a concentration of asphaltene dispersant additives for adding to a hydrocarbon-containing material, wherein the selection of the concentration of the asphaltene dispersant additives comprises receiving data corresponding to the effectiveness of the concentration of asphaltene dispersant additives for inhibiting or preventing asphaltene precipitation in a hydrocarbon-containing material subjected to elevated temperature and pressure conditions; wherein the data is derived from:
  - (i) subjecting a first column having an inert packing material therein to a first set of elevated temperature and pressure conditions;
  - (ii) precipitating an amount of asphaltenes from a first hydrocarbon-containing material sample having solvated asphaltenes therein with one or more first asphaltene-precipitating mobile phase solvents and capturing the precipitated asphaltenes in the inert packing material in the first column;
  - (iii) dissolving an amount of the precipitated asphaltenes at predetermined temperature with one or more second solvents having a solubility parameter of at least about 21 $MPa^{0.5}$ but no greater than about 30 $MPa^{0.5}$ to elute a fraction having dissolved asphaltenes therein;
  - (iv) determining the asphaltene content of the first sample by the concentration of asphaltenes in the eluted fraction from the first column;
  - (v) subjecting the first column or a second column having an inert packing material therein to a second set of elevated temperature and pressure conditions;
  - (vi) precipitating an amount of asphaltenes from a second hydrocarbon-containing material sample containing one or more asphaltene dispersant additives and having solvated asphaltenes therein with one or more second asphaltene-precipitating mobile phase solvents and capturing the precipitated asphaltenes in the inert packing material in the second column;
  - (vii) dissolving an amount of the precipitated asphaltenes at predetermined temperature with one or more second solvents having a solubility parameter of at least about 21 $MPa^{0.5}$ but no greater than about 30 $MPa^{0.5}$ to elute a fraction having dissolved asphaltenes therein;
  - (viii) determining the asphaltene content of the second sample by the concentration of asphaltenes in the eluted fraction from the second column; and
  - (ix) comparing the asphaltene content of the first sample with the asphaltene content of the second sample; and
- (b) injecting the selected concentration of asphaltene dispersant additives into the well, wellhead, a production line proximate the wellhead or a refinery line susceptible to fouling.

The method of the present invention advantageously determines the effectiveness of one or more asphaltene dispersant additives for inhibiting or preventing asphaltene precipitation in a hydrocarbon-containing material subjected to elevated temperature and pressure conditions in a simple, cost efficient and repeatable manner. In this way, the leading candidate asphaltene dispersant additives can be added to the one or more hydrocarbon-containing material which have been or are being subjected to elevated temperature and pressure conditions in order to, for example, (1) improve flow of a hydrocarbon-containing feedstock from a well, wellhead or a production line proximate the wellhead or (2) reduce fouling in one or more crude hydrocarbon refinery components located within a refinery.

DETAILED DESCRIPTION OF THE PREFERRED EMBODIMENTS

Figure 1:
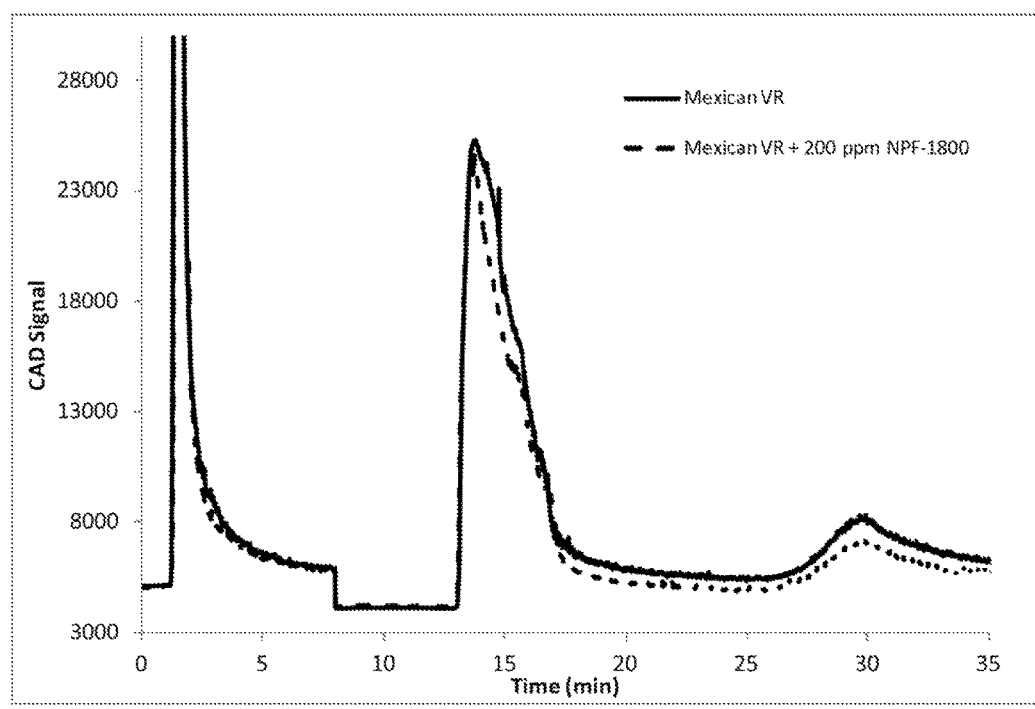
FIG. 1 is a LC-Trace showing the effect of adding 200 ppm of an asphaltene dispersant additive to a Mexican vacuum residue (1000+° F.) at 195° C.

In one embodiment, a method of the present invention determines the effectiveness of one or more asphaltene dispersant additives for inhibiting or preventing asphaltene precipitation in a hydrocarbon-containing material subjected to elevated temperature and pressure conditions. In general, the method involves the steps of: (a) subjecting a first column having an inert packing material therein to a first set of elevated temperature and pressure conditions; (b) precipitating an amount of asphaltenes from a first hydrocarbon-containing material sample having solvated asphaltenes therein with one or more first asphaltene-precipitating mobile phase solvents and capturing the precipitated asphaltenes in the inert packing material in the first column; (c) dissolving an amount of the precipitated asphaltenes at predetermined temperature with one or more second solvents having a solubility parameter of at least about 21 $MPa^{0.5}$ but no greater than about 30 $MPa^{0.5}$ to elute a fraction having dissolved asphaltenes therein; (d) determining the asphaltene content of the first sample by the concentration of asphaltenes in the eluted fraction from the first column; (e) subjecting the first column or a second column having an inert packing material therein to a second set of elevated temperature and pressure conditions; (f) precipitating an amount of asphaltenes from a second hydrocarbon-containing material sample containing one or more asphaltene dispersant additives and having solvated asphaltenes therein with one or more second asphaltene-precipitating mobile phase solvents and capturing the precipitated asphaltenes in the inert packing material in the second column; (g) dissolving an amount of the precipitated asphaltenes at predetermined temperature with one or more second solvents having a solubility parameter of at least about 21 $MPa^{0.5}$ but no greater than about 30 $MPa^{0.5}$ to elute a fraction having dissolved asphaltenes therein; (h) determining the asphaltene content of the second sample by the concentration of asphaltenes in the eluted fraction from the second column; and (i) comparing the asphaltene content of the first sample with the asphaltene content of the second sample.

Generally, the source of the hydrocarbon-containing material may be any source wherefrom a hydrocarbon-containing material such as a hydrocarbon crude may be obtained, produced, or the like. The source may be one or more producing wells in fluid communication with a subterranean oil reservoir. The producing well(s) may be under thermal recovery conditions, or the producing well(s) may be in a heavy oil field where the hydrocarbon crude or oil is being produced from a reservoir having a strong water-drive.

In one embodiment, the hydrocarbon-containing material sample includes any heavy hydrocarbons such as heavy crude oil, heavy hydrocarbons extracted from tar sands, commonly called tar sand bitumen, such as Athabasca tar sand bitumen obtained from Canada, heavy petroleum crude oils such as Venezuelan Orinoco heavy oil belt crudes, Boscan heavy oil, Hamaca crude oil, heavy hydrocarbon fractions obtained from crude petroleum oils, particularly heavy vacuum gas oils, vacuum residuum as well as petroleum tar, tar sands and coal tar. Other examples of heavy hydrocarbon material which can be used are oil shale, shale, coal liquefaction products and the like.

In another embodiment, the hydrocarbon-containing material sample includes any processed sample such as heavy cycle gas oil (HCGO), LC Fining products, fluid catalytic cracking (FCC) products and the like.

In one embodiment, a liquid sample of a hydrocarbon-containing material having solvated asphaltenes therein is provided. As one skilled in the art will readily understand, it may be necessary to add a solvent to the hydrocarbon-containing material in order for the sample to be sufficiently fluid enough to be passed through the column. Useful solvents include any solvent in which the hydrocarbon-containing material sample is soluble or which is capable of allowing the hydrocarbon-containing material sample to be sufficiently fluid to be passed through the column. Representative examples of such solvents include one or more chlorinated hydrocarbon solvents, one or more aromatic hydrocarbon solvents, one or more ether solvents, one or more alcohol solvents and the like and mixtures thereof.

Suitable chlorinated hydrocarbon solvents include, but are not limited to, dichloromethane, 1,2-dichloroethane, chloroform, carbon tetrachloride and the like and mixtures thereof. Suitable aromatic hydrocarbon solvents include, but are not limited to, benzene, toluene, xylene and the like and mixtures thereof. Suitable ether solvents include tetrahydrofuran, diethylether, dioxane and the like and mixtures of thereof. Suitable alcohol solvents include low molecular weight aliphatic alcohols such as methanol, ethanol, isopropanol and the like and mixtures thereof.

In one embodiment, the sample solution can be prepared from about 10 to about 50 wt. % solution of the hydrocarbon-containing material sample in the solvent(s).

Initially, a first column is provided which is subjected to a first set of elevated temperature and pressure conditions as discussed below. Generally, the column will have an inlet and an outlet and can be any type of column which is hollow and permits the flow of an aqueous-type material through the interior of the column. The column can be any size and cross sectional shape, e.g., the column can be cylindrical, square, rectangular, triangular, or any other geometrical shape as long as it is hollow and permits the passing of aqueous-type material. In one embodiment, the column is cylindrical. Furthermore, the column can be of any suitable length and any inner diameter or inner cross-sectional area. In one embodiment, the column can have a diameter of from about 0.25 inches to about 1 inch and a length of from about 50 mm to about 500 mm. One skilled the art could envisage that the column can generally be any inert filtration device for use in the methods of the present invention.

Any suitable material may be selected for use as the column. For example, the column can be formed of a relatively inert or chemically unreactive material such as glass, stainless steel, polyethylene, polytetrafluoroethylene (PTFE), polyaryletheretherketone, (PEEK), silicon carbide or mixtures of thereof, for example, a PEEK-lined stainless steel column.

The column may be vertical or horizontal or arranged in any suitable way, provided that it can be loaded with the sample solution and that the appropriate solvent(s) can be passed through it. As will be understood by those of ordinary skill in the art, a pump may also be used to increase the flow rate through the column.

An inert packing material is included within the column. As one skilled in the art will readily appreciate, the amount of the inert packing material should not exceed an amount which will prevent the passing of any liquid containing material through the column. The packed column advantageously allows for the use of a relatively small volume of sample solution and solvent(s). Suitable inert packing material includes any material that is inert to asphaltene irreversible adsorption. Examples of such materials include fluorinated polymers such as, for example, polyvinylidene fluoride (PVDF), fluorinated ethylene propylene (FEP), polytetrafluoroethylene (PTFE), silicon carbide, polydivinylbenzene (PDVB) and the like and mixtures thereof.

Before the sample solution has been passed into the column, the column is subjected to a first set of elevated temperature and pressure conditions. In this way, the hydrocarbon-containing material can be evaluated for any asphaltene precipitation in both upstream and downstream applications, i.e., at reservoir or process conditions, in order to minimize problems associated with asphaltene precipitation during the upstream and downstream applications. For example, a hydrocarbon-containing feedstock obtained from one more producing wells in fluid communication with a subterranean oil reservoir under thermal recovery conditions can be evaluated. Thermal recovery conditions ordinarily includes temperatures ranging from about 30° C. to about 140° C. and pressures ranging from about 30 psi to about 15,000 pound per square inch (psi) (i.e., from about 2 to about 1020 atmospheric pressure (atm)).

In another example, a hydrocarbon-containing material that has been subjected to processing conditions can be evaluated. Processing conditions include, by way of example, conditions associated with a hydrocarbon-containing material during hydroprocessing, e.g., hydroconversion, hydrocracking, hydrotreating, hydrogenation, hydrofinishing and hydroisomerization. Hydroprocessing conditions ordinarily includes temperatures ranging from about 200° C. to about 450° C. and pressures ranging from about 300 psi and up to about 4500 psi (i.e., from about 20 to about 306 atm).

For example, the column is subjected to a first set of elevated temperature and pressure conditions by placing it in an oven and heated and pressurized to a suitable temperature and pressure. A suitable elevated temperature will ordinarily range from about 30 to about 450° C. A suitable elevated pressure will ordinarily range from about 1 to about 1020 atm. The oven can be heated by means of an electrical resistance and the desired pressure is achieved by using, for example, a back pressure regulator. Also, a liquid pump is typically used to pump the sample into the liquid column. As one skilled in the art will readily appreciate, the type of oven and liquid pump to pump the sample will depend on, for example, the desired temperature and pressure for the test. In other words, the oven and pump design are based on your target reservoir and refinery conditions. A suitable oven for use herein can be any conventional high pressure liquid chromatography (HPLC) oven such as those which are commercially available from such sources as Selerity Technologies (Salt Lake City, Utah), e.g., Polaratherm™ Series 9000 liquid chromatograph, and Agilent Technologies (Santa Clara, Calif.), e.g., Agilent 1290 Series infinity system.

The HPLC system might further comprise a sampling unit for introducing the sample liquid into the mobile phase stream, a detector for detecting separated compounds of the sample liquid, a fractionating unit for outputting separated compounds of the sample liquid, or any combination thereof. Further details of HPLC system are disclosed with respect to the aforementioned Selerity Technologies and Agilent Technologies HPLC series, under www.selerity.com and www.agilent.com, respectively, which shall be incorporated herein by reference.

Embodiments of the invention can be partly or entirely embodied or supported by one or more suitable software programs, which can be stored on or otherwise provided by any kind of data carrier, and which might be executed in or by any suitable data processing unit. Software programs or routines can be preferably applied in or by a control unit.

The asphaltenes are then precipitated from the hydrocarbon-containing material sample with one or more first asphaltene-precipitating mobile phase solvents and captured in the inert packing material in the column. Useful asphaltene-precipitating mobile phase solvent(s) can be determined by one skilled in the art. In one embodiment, the asphaltene-precipitating mobile phase solvent is n-heptane. However, other asphaltene-precipitating mobile phase solvents such as, for example, n-pentane or n-hexane may be used.

In one embodiment, the sample solution is passed into the column, and then one or more first asphaltene-precipitating mobile phase solvents are passed through the column. The one or more first asphaltene-precipitating mobile phase solvents should be passed into the column for a time period sufficient to elute the soluble fraction, commonly known as maltenes or petrolenes, and induce precipitation of the insoluble fraction, i.e., the precipitated asphaltenes, from the hydrocarbon-containing material sample. Generally, once the asphaltene-precipitating mobile phase solvent (i.e., one or more first solvents) enters the column, the asphaltene-precipitating mobile phase solvent dilutes and displaces the solvent in the sample solution, thereby allowing the asphaltenes to substantially precipitate therefrom. The soluble fraction then elutes from the column.

In another embodiment, the hydrocarbon-containing material sample is first combined with one or more first asphaltene-precipitating mobile phase solvents to induce precipitation of the insoluble fraction, i.e., the precipitated asphaltenes, from the hydrocarbon-containing material sample and form a soluble fraction. The solution is then passed into the column such that the precipitated asphaltenes are captured in the inert packing material and the soluble fraction is eluted through the column.

Next, the precipitated asphaltenes are dissolved at a predetermined temperature once substantially all of the e soluble fraction has eluted. In general, once substantially all of the soluble fraction has eluted, the column is allowed to reach a predetermined temperature while the pressure is maintained. The predetermined temperature is a temperature equal to or below the temperature of the column. In one preferred embodiment, the predetermined temperature is at room temperature, i.e., about 20-30° C. To allow the predetermined temperature to reach a predetermined temperature, the column can be cooled naturally or through a refrigerant such as nitrogen or liquid carbon dioxide. The precipitated asphaltenes are then dissolved employing one or more first solvents having a solubility parameter of at least about 21 $MPa^{0.5}$ but no greater than about 30 $MPa^{0.5}$. A solubility parameter as described herein is determined by the Hansen's methodology described in Barton, A. F. M. *Handbook of Solubility Parameters and Other Cohesion Parameters*; CRC Pres Inc.: Boca Raton, Fla., p. 95 (1983).

Suitable one or more first solvents having a solubility parameter of at least about 21 $MPa^{0.5}$ but no greater than about 30 $MPa^{0.5}$ can be determined by one skilled in the art. Generally, the one or more first solvents will dissolve substantially all of the precipitated asphaltenes in the column. Useful solvents include, but are not limited to, one or more alcohol solvents, one or more chlorinated hydrocarbon solvents, one or more aromatic solvents, one or more ether solvents and the like and mixtures thereof. Representative examples of such solvents can be one or more of any of those disclosed above as long as the one or more first solvents have a solubility parameter of at least about 21 MPa$^{0.5}$ but no greater than about 30 MPa$^{0.5}$. It is also contemplated that blends of such solvents can be used. In one embodiment, a blend can contain from about 0.5 wt. % to about 99.5 wt. % chlorinated solvent and from about 99.5 wt. % to about 0.5 wt. % alcohol solvent. In another embodiment, a blend can contain from about 80 wt. % to about 95 wt. % chlorinated solvent and from about 20 wt. % to about 5 wt. % alcohol solvent.

The asphaltene concentration in the eluted fractions from the column is continuously monitored using, for example, a liquid chromatography detector which generates a signal proportional to the amount of each eluted fraction and is recorded in a manner well known in the art. There are a number of commercially available liquid chromatography detectors that can be used including, e.g., refractive index detectors, mass spectrometry, liquid chromatography/mass spectrometry, NMR spectroscopy, Raman spectroscopy, infrared spectroscopy, fluorescence spectroscopy, UV-Vis spectroscopy, diode array detector, charged aerosol detector, evaporative light scattering detectors (ELSD) and the like; all of which can be used in the methods described herein. Other online detectors are known to those skilled in the art.

In one preferred embodiment, a charged aerosol detector (CAD) is used as a liquid chromatography detector to monitor each eluting sample's concentration to determine the solubility characteristics of the precipitated asphaltenes. A suitable CAD can be any CAD commercially available from such sources as Thermo Scientific (Waltham, Mass.), e.g., Dionex Corona™ ultra RS™ Charged Aerosol Detector. The operating principle of a charged aerosol detector is as follows: The sample is nebulized into droplets, which are subsequently dried into particles. The particle size increases with the amount of sample. A stream of positively charged gas collides with the sample particles. The charge is then transferred to the particles. These particles are transferred to a collector where the charge is measured by a highly sensitive electrometer. This generates a signal in direct proportion to the quantity of sample present. For example, in the case of the asphaltenes, the result is a single peak for the eluted solvent fraction. The area under the asphaltene peak is then measured using conventional high pressure liquid chromatography (HPLC) software packages, Chemstation® by Agilent Technologies (Santa Clara, Calif.), and this area is directly proportional to the asphaltene concentration. For example, the Chemstation software program determines a response factor relating peak area intensity to the amount of grams for each calibrated asphaltene. The software then determines the number of grams of the calibrated asphaltene from the response factor and the peak area.

Once the asphaltene concentration in the eluted fraction has been determined, a second hydrocarbon-containing material sample having solvated asphaltenes therein is provided. Typically, the second hydrocarbon-containing material sample is from the same batch as the first hydrocarbon-containing material sample. Alternatively, the second hydrocarbon-containing material sample can be a sample obtained from the same source as the first hydrocarbon-containing material sample.

Next, one or more asphaltene dispersant additives are added to the second hydrocarbon-containing material sample. The one or more asphaltene dispersant additives can be any presently known or later-discovered asphaltene dispersant additive, e.g., U.S. Patent Application Publication Nos. 20040039125, 20040050752, 20040163995, 20040232042, 20040232043, 20040232044, 20040238404, 20050082231, 20050091915, 20060079434, 20060096757, and 20060096758; International Patent Applications Nos. 200174966, 2004033602, 2005010126, 2005054321, and 2006047745; Russian Patent Nos. 2172817, 2173320, 2185412, 2220999, 2223294, 2237799, 2250247, 2261887, and 2261983; Canadian Patent No. 2326288; European Patent No. 1091085; European Patent Application No. 2006795579; and Mexican Patent Application No. 2001013139, the contents of each of which are incorporated by reference herein.

In one embodiment, an asphaltene dispersant additive includes one or more fatty acid esters, one or more lactic acid esters, and mixtures thereof. Suitable fatty acid esters include, by way of example, $C_1$ to $C_4$ esters of $C_{16}$ to $C_{20}$ fatty acids including edible vegetable oils. Such oils may have a melting point of $-10°$ C. or less. Useful edible vegetable oils include corn, coconut, mustard, palm kernel oil, neem, niger seed, olive, peanut, poppy seed, safflower, rapeseed, sesame, soybean, sunflower seed, wheat germ oil and other polyunsaturated containing oils (such as oleic acid, linoleic acid, erucic acid, and linolenic acid). The $C_{16}$ to $C_{20}$ fatty acid ester may further be a mixture of oils. Edible vegetable oils containing a mixture of about 70 to about 90 weight percent oleic and linoleic acids are often preferred.

Suitable lactic acid esters include a $C_1$ to $C_4$ ester of lactic acid. Exemplary $C_1$ to $C_4$ alcohols for producing the lactic acid ester include methanol, ethanol, propanol, isopropanol, allyl alcohol, butanol, 3-buten-1-ol, t-butanol and sec-butanol. In one embodiment, the lactic acid ester is ethyl lactate. Ethyl lactate is the ester of natural lactic acid produced by fermentation of corn-derived feedstock. As with the fatty acid esters, lactic acid esters are 100% biodegradable, breaking down into carbon dioxide and water, non-toxic, and renewable.

In another embodiment, an asphaltene dispersant additive includes a composition comprising: (i) a chelating aminocarboxylic acid-$C_8$ to $C_{22}$ amine complex; (ii) a $C_{15}$ to $C_{21}$ bis(2-hydroxyethyl)amide; and (iii) a $C_{15}$ to $C_{44}$ imidazoline compound. The chelating aminocarboxylic acid-$C_8$ to $C_{22}$ amine complexes are generally formed by heating the $C_8$ to $C_{22}$ amine with the chelating aminocarboxylic acid. The amounts of amine and chelating aminocarboxylic acid used to form the complexes can vary greatly, depending on several factors such as the particular application, and the composition and physical properties of the heavy crude oil (HCO) or other petroleum product; however, in general the molar equivalent ratio of amine to acid equivalent of chelating aminocarboxylic acid can be in the range of about 10:1 to about 1:2. A chelating aminocarboxylic acid is a compound having an amine group, and having at least two carboxylic acid groups that can form coordinate bonds to a single metal atom. Suitable chelating aminocarboxylic acids include, by way of example, ethylenediaminetetraacetic acid (EDTA), hydroxyethylethylenediaminetriacetic acid, nitrilotriacetic acid (NTA), N-dihydroxyethylglycine and ethylenebishydroxyphenyglycine.

Suitable $C_8$ to $C_{22}$ amines include n-octylamine, 2-ethylhexylamine, t-octylamine, n-decylamine, tertiary-alkyl primary amines (either singly or in any combinations thereof), tridecylamine, n-undecylamine, lauryl amine, hexadecylamine, heptadecylamine, octadecylamine, decenylamine, dodecenylamine, palmitoleylamine, oleylamine, linoleylamine, eicosenylamine and polyetheramine; and polyalkylamines such as polyisobutyleneamine. Commercially available mixtures of suitable primary aliphatic amines in the $C_{12}$ to $C_{18}$ range include ARMEEN O and ARMEEN OD (Akzo Nobel; Stratford, Conn.). It is preferred to use oil-soluble aliphatic amines in which the aliphatic group is a tertiary aliphatic group, most preferably a tertiary alkyl group, e.g., tertiary-alkyl primary amines. Commercially available mixtures of tertiary-alkyl primary amines include 1,1,3,3-tetramethylbutylamine (PRIMENE TOA); an isomeric mixture of $C_{16}$ to $C_{22}$ tertiary alkyl primary amines (PRIMENE JM-T), an isomeric mixture of $C_8$ to $C_{10}$ tertiary alkyl primary amines (PRIMENE BC-9); an isomeric mixture of $C_{10}$ to $C_{15}$ tertiary alkyl primary amines (PRIMENE 81-R); or mixtures thereof. (Rohm and Haas Company; Philadelphia, Pa.).

A suitable $C_{15}$ to $C_{21}$ bis(2-hydroxyethyl)amide is represented by the following formula (I)

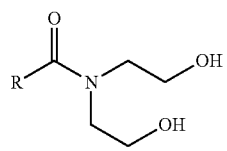

(I)

wherein R is $C_{15}$ to $C_{21}$ alkyl, $C_{15}$ to $C_{21}$ alkenyl, or a mixture thereof For the $C_{15}$ to $C_{44}$ imidazoline compound, the imidazoline ring has at least one $C_{15}$ to $C_{22}$ alkyl or alkenyl side chain. In one embodiment, the imidazoline ring also has an alkenylamide side chain having from 10 to 24 carbon atoms. In one embodiment, the $C_{15}$ to $C_{44}$ imidazoline compound is a $C_{30}$ to $C_{44}$ imidazoline compound. In another embodiment, the imidazoline compound is a reaction product of a fatty acid and a polyamine. Suitable polyamines include, by way of example, ethylenediamine, diethylenetriamine, and hydroxyethyl ethylenediamine. Suitable fatty acids include, by way of example, $C_{12}$ to $C_{20}$ alkyl and/or alkenyl carboxylic acids, including polyunsaturated acids. Suitable fatty acids include oleic, linoleic and fatty acid mixtures derived from tall oil, soybean or palm oils. Preparation of fatty acid-polyamine reaction products is known, and is disclosed, e.g., in WO 01/25214.

In general, the composition can contain from about 10 to about 80% of a chelating aminocarboxylic acid-$C_8$ to $C_{22}$ amine complex, about 10 to about 80% of a $C_{15}$ to $C_{21}$ bis(2-hydroxyethyl)amide, and about 15 to about 80% of a $C_{15}$ to $C_{44}$ imidazoline compound, with all amounts being exclusive of solvents.

In another embodiment, an asphaltene dispersant additive includes at least one compound of the general formula (II)

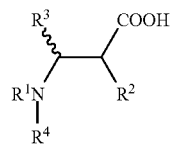

(II)

or a zwitterionic form or salt thereof, wherein $R^1$ is $C_{10}$ to $C_{22}$ alkyl or aralkyl; $R^2$ and $R^3$ independently are hydrogen or $C_1$ to $C_4$ alkyl; $R^4$ is hydrogen, $C_1$ to $C_{22}$ alkyl, $C_7$ to $C_{22}$ alkyl or —CH($R^5$)CH($R^6$)COOH, wherein $R^5$ and $R^6$ independently are hydrogen or $C_1$ to $C_4$ alkyl. Typically, a compound of formula (II) results from reaction of a primary or secondary amine with an unsaturated acid such as acrylic acid, methacrylic acid or crotonic acid, or combinations thereof. Formation of a 1:1 adduct of a primary amine and an unsaturated acid results in a product in which $R^4$ is hydrogen. A 1:2 adduct has $R^4$ equal to —CH($R^5$)CH($R^6$)COOH. An adduct of a secondary amine and an unsaturated acid has $R^4$=$C_{10}$ to $C_{22}$ alkyl or alkyl. In one embodiment, $R^1$ is derived from an unsubstituted $C_{10}$ to $C_{22}$ alkyl amine, $R^1NH_2$, preferably one which is an oil-soluble amine. In one embodiment, the alkyl amine is a tertiary alkyl primary amine, i.e., a primary amine in which the alkyl group is attached to the amino group through a tertiary carbon. Examples of commercially available tertiary alkyl primary amines are the Primene™, amines available from Rohm and Haas Company, Philadelphia, Pa.

In another embodiment, an asphaltene dispersant additive includes at least one reaction product of (a) an amine; and (b) a carboxylic, phosphonic or sulfonic acid. The reaction product has no new covalent bonds. i.e., bonds not present in the amine or the acid. The reaction product is either a salt or a physical mixture or complex of the amine and the acid. In one embodiment, a reaction product used in this invention is a salt, preferably one that is soluble in oil at least at the aforementioned levels. In one embodiment, the salt has at least ten carbon atoms, more preferably at least 15 carbon atoms. The salt, when used in this invention, has a cation and an anion, and is not zwitterionic. In one embodiment, the acid is a carboxylic acid having no other acidic functional groups, i.e. groups having $pK_a<6$. In another embodiment, the acid is a phosphonic acid having no other acidic functional groups. In another embodiment, the acid is a sulfonic acid having no other acidic functional groups.

In another embodiment, an asphaltene dispersant additive includes at least one reaction product of (a) an imine; and (b) an organic acid. In one embodiment in which the organic acid is a carboxylic, phosphonic or sulfonic acid, the separation between a polar group and a carboxylate, phosphonate or sulfonate ion (collectively: "conjugate base group"); or a protonated imine ("conjugate acid group"); is measured by the number of covalent chemical bonds intervening between either: (i) the atom of the polar group through which it is attached (e.g., the oxygen of hydroxy; the nitrogen of amino or nitroso; or the sulfur of sulfur-containing groups); or (ii) a carbonyl or imine carbon of the polar group (e.g., the carbonyl carbon of amide or the imine carbon of oxime); and one of: the carboxylate carbon, the phosphorus atom of a phosphonate, the sulfur atom of a sulfonate and the imine nitrogen atom. For example, in an imine salt of glycolic acid (hydroxyacetic acid), the oxygen of the hydroxy group is two bonds from the carbonyl carbon of the carboxylate group. Preferably, at least one polar group in a compound of this invention is located two to eight chemical bonds from either a conjugate acid or base functional group, more preferably from two to seven chemical bonds, and most preferably two, three, four, five or six chemical bonds from either a conjugate acid or base functional group.

In another embodiment, an asphaltene dispersant additive includes at least one compound having: (i) at least one carboxyl group; (ii) at least one amide group; and (iii) at least fifteen carbon atoms. In one embodiment, the compound is not in the form of a salt having an anion and a cation, i.e., a salt that is not a zwitterion; more preferably the compound is a neutral compound. In one embodiment, a carboxyl or amide functional group is not part of a heterocyclic ring. In one embodiment, the compound is aliphatic. In one embodiment, the compound is acyclic. In one embodiment, the compound is represented by formula (III)

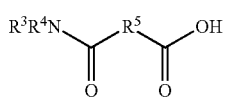

(III)

wherein $R^5$ is $C_1$ to $C_{70}$ difunctional alkyl or $C_6$ to $C_{14}$ difunctional aryl, and $R^3$ and $R^4$ independently are hydrogen or organic functional groups. Preferably, $R^3$ and $R^4$ independently are hydrogen, alkyl, heteroalkyl, heterocyclic, aryl or aralkyl. Preferably, at least one $R^3$, $R^4$ and $R^5$ has at least 12 carbon atoms.

In another embodiment, an asphaltene dispersant additive includes non-sulfonated and sulfonated alkyl phenol formaldehydes. In one embodiment, the sulfonated alkyl phenol formaldehydes are products obtainable by sulfonation of compounds corresponding to formula (IV) or (V):

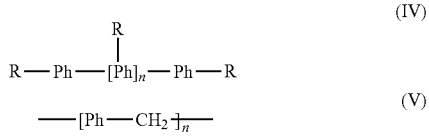

in which n is a number of 2 to 12 and R is a $C_3$ to $C_{24}$ alkyl, $C_6$ to $C_{12}$ aryl or hydroxyaryl or $C_7$ to $C_{12}$ alkyl group. In addition, Ph in formula (I) and (II) is a phenol residue.

The sulfonation products are obtained by sulfonation of compounds known per se corresponding to general formulae (IV) and/or (V). These starting products are known, for example, from DE 197 09 797 A1. Reference is made here to formulae (IV) and (V) in claim 1 of DE 197 09 797 A1, to the disclosure on page 2, lines 40 to 44 and to the disclosure on page 3 of that document. The disclosures of those passages are specifically included in the disclosure of the present application. Formulae (IV) and (V) in DE 197 09 797 are identical with those of the present application. The compounds in question are resins which are obtainable, for example, under the name of Dowfax DM 645 (Dow Chemicals).

The educts corresponding to formulae (IV) and (V) are sulfonated in a known manner with gaseous $SO_3$. The sulfonation products are not neutralized, but are present as free acids. The sulfonation of the educts can be carried out by a continuous process in a falling film reactor. The gaseous sulfur trioxide is produced in situ by pyrolysis of pure sulfur. The polyalkyl formaldehyde resin used is preferably reacted with sulfur trioxide in an equimolar ratio. The reaction itself advantageously takes place at a temperature of 75 to 80° C. The end product is preferably not neutralized. The sulfonation products are obtained in the form of aqueous solutions which may be directly formulated and used as asphaltene dispersants without any further steps.

In another embodiment, an asphaltene dispersant additive includes a compound of formula (VI):

(VI)

wherein A is an optionally substituted ring system containing 6 to 14 carbon atoms; n is at least 1 and may equal the number of positions available for substitution in A; each X is independently a linker group; and each R is independently a hydrocarbyl group containing 10 to 25 carbon atoms. The compound of formula (I) is an amphiphilic molecule primarily consisting of two active parts; an adsorbing part (ring system A), which sticks to the surface of the asphaltene particle and which carries a long chain (X—R) attached to the ring. A is a primarily aromatic, largely flat molecule whose ring(s) give sufficient interactions through van der Waal's forces to attach itself to the similarly aromatic asphaltene. Thus it provides an anchor for the chain which is much longer and extends into the oil. The chain, being primarily aliphatic, is surrounded by a good solvent, such as oil, and adopts an attitude with many possible conformations while attached to the asphaltene particle at one end through the ring system A.

In one embodiment, A is naphthalene, X is selected from a $C_1$ to $C_4$ alkyl ether group, a $C_1$ to $C_4$ alkyl thio group and a $C_1$ to $C_4$ alkyl amino group, n is 1 and R is a $C_{12}$ to $C_{16}$ alkyl chain. In another embodiment, A is naphthalene, X is selected from an ether link, an amine link or a thio ether link, n is 1 and R is a $C_{14}$ to $C_{18}$ alkyl chain. In another embodiment, A is naphthalene, X is selected from an ether link, an amine link or a thio ether link, n is 1 and R is a $C_{16}$ alkyl chain. In another embodiment, A is naphthalene, X is an ether link, n is 1 and R is n-hexadecyl.

In another embodiment, an asphaltene dispersant additive includes a dendrimeric compound. Dendrimeric compounds are in essence three-dimensional, highly branched oligomeric or polymeric molecules comprising a core, a number of branching generations and an external surface composed of end groups. A branching generation is composed of structural units, which are bound radially to the core or to the structural units of a previous generation and which extend outwards. The structural units have at least two reactive mono-functional groups and/or at least one mono-functional group and one multifunctional group. The term multifunctional is understood as having a functionality of 2 or higher. To each functionality a new structural unit may be linked, a higher branching generation being produced as a result. The structural units can be the same for each successive generation but they can also be different. The degree of branching of a particular generation present in a dendrimeric compound is defined as the ratio between the number of branchings present and the maximum number of branchings possible in a completely branched dendrimer of the same generation. The term functional end groups of a dendrimeric compound refer to those reactive groups which—form part of the external surface. Branchings may occur with greater or lesser regularity and the branchings at the surface may belong to different generations depending on the level of control exercised during synthesis. Dendrimeric compounds may have defects in the branching structure, may also be branched asymmetrically or have an incomplete degree of branching in which case the dendrimeric compound is said to contain both functional groups and functional end groups.

Dendrimeric compounds as referred to hereinabove have been described in, for example, International Patent Application Publications Nos. WO 93/14147 and WO 97/19987 and in Dutch Patent Application No. 9200043. Dendrimeric compounds have also been referred to as "starburst conjugates", see, for example, International Patent Application Publication No. WO 88/01180. Such compounds are described as being polymers characterised by regular dendrimeric (tree-like) branching with radial symmetry.

Functionalized dendrimeric compounds are characterized in that one or more of the reactive functional groups present in the dendrimeric compounds have been allowed to react with active moieties different from those featuring in the structural units of the starting dendrimeric compounds. These moieties can be selectively chosen such that, with regard to its ability to solubilize asphaltenes, the functionalized dendrimeric compound outperforms the dendrimeric compound.

The hydroxyl group is one example of a functional group and functional end group of a dendrimeric compound. Dendrimeric compounds containing hydroxyl groups can be functionalized through well-known chemical reactions such as esterification, etherification, alkylation, condensation and the like. Functionalized dendrimeric compounds also include compounds that have been modified by related but not identical constituents of the structural units such as different amines, which as such may also contain hydroxyl groups.

A preferred class of dendrimeric compounds capable of solubilizing asphaltenes comprises the so-called hyperbranched polyesteramides, commercially referred to as HYBRANES™ (the word HYBRANE is a trademark). The preparation of such compounds has been described in more detail in International Patent Application Nos. WO-A-99/16810, WO-A-00/58388 and WO-A-00/56804. Accordingly, the dendrimeric compound is preferably a condensation polymer containing ester groups and at least one amide group in the backbone, having at least one hydroxyalkylamide end group and having a number average molecular weight of at least 500 g/mol. This class of polymers has a lower degree of branching than the poly(propylene imine) dendrimers described in WO-A-93/14147, but still retains the non-linear shape and the high number of reactive end groups, which are characteristic of dendrimeric compounds. Compounds belonging to this class of dendrimers are suitably produced by reacting a cyclic anhydride with an alkanolamine, giving rise to dendrimeric compounds by allowing them to undergo a number of (self-) condensation reactions leading to a predetermined level of branching. It is also possible to use more than one cyclic anhydride and/or more than one alkanolamine.

The alkanolamine may be a dialkanolamine, a trialkanolamine or a mixture thereof. Examples of suitable dialkanolamines are 3-amino-1,2-propanediol, 2-amino-1,3-propanediol, diethanolamine bis(2-hydroxy-1-butyl)amine, dicyclohexanolamine and diisopropanolamine. An example of a suitable trialkanolamine is tris(hydroxymethyl)amino methane or triethanolamine.

Suitable cyclic anhydrides comprise succinic anhydride, glutaric anhydride, tetrahydrophthalic anhydride, hexahydrophthalic anhydride, phthalic anhydride, norbornene-2,3-dicarboxylic anhydride, and naphthalenic dicarboxylic anhydride. The cyclic anhydrides may contain substituents, in particular hydrocarbon (alkyl or alkenyl) substituents. The substituents suitably comprise from 1 to 15 carbon atoms. In another embodiment the cyclic anhydride contains a polyalkenyl substituent. Suitably, the alkene from which the polyalkylene chain has been built is an ethylenically unsaturated hydrocarbon containing from 2 to 10, preferably from 2 to 6 carbon atoms. The alkene is suitably ethene, propene, butene, isobutene, pentene or hexene. Most preferred is a poly(isobutenyl) chain as substituent. The chain may have various lengths. Good results are obtainable with substituents comprising from 6 to 50 alkene monomers. More preferred is a chain with from 10 to 40 alkene monomers. Suitable non-polymeric examples of substituted cyclic anhydrides include. 4-methylphthalic anhydride, 4-methyl tetrahydro- or 4-methylhexahydrophthalic anhydride, methyl succinic anhydride and 2-dodecenyl succinic anhydride. Mixtures of anhydrides can also be used.

In one embodiment, a mixture of succinic anhydride and poly(isobutenyl)succinic anhydride is used. The molar ratio between succinic anhydride to poly(isobutenyl)-succinic anhydride suitably ranges from 1:9 to 9:1, preferably from 2:3 to 9:1. The self-condensation reaction is suitably carried out without a catalyst at temperatures between 100 and 200° C. By carrying out such self-condensation reactions compounds will be obtained having amide-type nitrogen moieties as branching points and with hydroxyl end groups in the base polymer. Depending on the reaction conditions, predetermined molecular weight ranges and number of end groups can be set. For instance, using hexahydrophthalic anhydride and di-isopropanolamine polymers can be produced having a number average molecular weight tuned between 500 and 50,000, preferably between 670 and 10,000, more preferably between 670 and 5000. The number of hydroxyl groups per molecule in such case is suitably in the range between 0 and 13.

The functional end groups, in particular hydroxyl groups, of the polycondensation products can be modified by further reactions as disclosed in the above-mentioned applications WO-A-00/58388 and WO-A-00/56804. Suitable modification can take place by partial replacement of the alkanolamine by other amines, such as secondary amines, e.g. N,N-bis-(3-dimethylaminopropyl)amine, morpholine or non-substituted or alkyl-substituted piperazine, in particular N-methyl piperazine. The use of N,N-bis-(dialkylaminoalkyl)amines results in dendrimeric polymers that have been modified to have tertiary amine end groups. In particular, the products prepared by the polycondensation of 2-dodecenyl succinic anhydride or hexahydrophthalic anhydride with di-isopropanolamine that have been modified by morpholine, tertiary amine or non-substituted or alkyl-substituted piperazine end groups are very suitable for use in the process of the present invention. A preferred type of modification can be obtained by reaction of at least part of the hydroxyl end groups with acids or acid anhydrides. In one embodiment, the hydroxyl groups can be modified by a reaction with an organic acid or an acid anhydride, such as with succinic anhydride, alkenyl succinic anhydride, hexahydrophthalic anhydride, coco fatty acid or lauric acid.

In another embodiment, an acid anhydride is used that contains a polyalkenyl substituent. Suitably, the alkene from which the polyalkylene chain has been built is an ethylenically unsaturated hydrocarbon containing from 2 to 10 carbon atoms. The alkene is suitably ethene, propene, butene, isobutene, pentene or hexene. Most preferred is a poly(isobutenyl) chain as substituent. The chain may have various lengths, e.g., substituents comprising from 6 to 50 alkene monomers. In one embodiment, a poly(isobutylene) chain as substituent to succinic acid anhydride is used. In this way the dendrimeric compound contains hydroxyl functional groups and carboxylic functional groups.

In another embodiment, an asphaltene dispersant additive includes a polyester amide obtainable by a two-stage reaction in which (A) a polyisobutylene is reacted with at least monounsaturated acids containing 3 to 21 carbon atoms or derivatives thereof, either (A.1) in the presence of radical initiators at temperatures of 65 to 100° C. or (A.2) without radical initiators, optionally catalyzed by Lewis acids, at 150 to 250° C., and (B) an alkylamine with the general formula R—NH$_2$, in which R is an alkyl group containing 1 to 4 carbon atoms, is added to the product thus obtained and the mixture is stirred at 60 to 100° C. and then cooled and the product is isolated in known manner.

The polyester amides are based on polyisobutylene, a raw material which is industrially obtained by polymerization of isobutylene. The polyisobutylenes can have molecular weights of 500 to 50,000, preferably in the range from 1,000 to 25,000 and more preferably in the range from 1,500 to 15,000. The polyisobutylenes are introduced into a reaction vessel at temperatures of at least 60° C. and the unsaturated acids are then added. These acids or their derivatives are at least mono-olefinically unsaturated and preferably contain 3 to 7 carbon atoms. The anhydrides are particularly preferred. A preferred anhydride is maleic anhydride. However, maleic acid or fumaric acid or their esters or acrylic acid, methacrylic acid and derivatives thereof are also suitable components in step (A).

In one embodiment, the reaction in the first step takes place in the presence of radical initiators, such as azo-bis-isobutyronitrile (AIBN), dibenzoyl peroxides, tert-amyl peroxy-2-ethylhexanoate, tert-butyl peroxi-2-ethylhexanoate, tert-butyl peroxyisobutyrate and tert-butyl monoperoxymaleate.

Alternatively, it is also possible to work without radical initiators. The reaction according to (A.2) systematically represents an "ene" reaction, it being possible to carry this out in the presence of catalysts selected from the group of Lewis acids. Suitable Lewis acids include, for example, the bromides of phosphorus and aluminum, the chlorides of boron, aluminum, phosphorus, bismuth, arsenic, iron, zinc and tin. However, it is preferred to work without Lewis acids and to react the reactants polyisobutylene and carboxylic acid directly with one another. The reaction temperature in the case of variant (A.2) is higher than for (A.1), namely in the range from 150 to 250° C.

Step (A) of the process takes place under an inert atmosphere, for example, argon or nitrogen. The ratio by weight of polyisobutylene to carboxylic anhydride will range from 200:1 to 1:200. The choice of suitable ratios by weight is governed by the molecular weight of the components used and may readily be made by the expert.

The reaction time is at least 3 hours at a temperature of at least 60° C. in the case (A.1) or at least 150° C. in the case (A.2), higher temperatures and longer reaction times, for example, 4 to 8 hours being preferred. Thereafter, a suitable amine with the formula R—NH$_2$ may be added to the reaction mixture. However, the reaction mixture may also first be freed from unreacted anhydride, preferably by distillation under reduced pressure, and the reaction mixture thus worked up subsequently reacted with the amine at a temperature of at least 50° C. Under the effect of the exothermic reaction of the polyisobutylene/anhydride product with the amine, the temperature in the reaction vessel rises to around 100° C. The mixture containing the end product then cools down again and may then be used without further purification. Process steps (A) and (B) may be carried out in a single reaction stage or in two separate stages either continuously or in batches.

The amines of the formula R—NH$_2$ are known compounds, such as monoethanolamine. The ratio by weight between polyisobutylene and amine can be between 100:1 and 10:1

In another embodiment, an asphaltene dispersant additive includes cardanol-aldehyde resins. In general, cardanol-aldehyde resins are obtainable by reacting cardanol with a compound of the formula (VII)

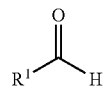
(VII)

in which $R^1$ is H, CHO, COOH, COOR$^2$ or $R^2$, and $R^2$ is a C$_1$ to C$_{30}$-alkyl, C$_2$ to C$_{30}$-alkenyl, C$_6$ to C$_{18}$-aryl or a C$_7$ to C$_{30}$-alkylaryl, and which have a number-average molecular weight of from 250 to 100 000 units. Cardanol is a constituent of oil that is obtained from the shell of cashew kernels.

In general, the one or more asphaltene dispersant additives will be added to the second hydrocarbon-containing material sample at a concentration of from about 0.1 to about 50,000 mg of asphaltene dispersant additive per kilogram of hydrocarbon-containing material sample.

The first column or a second column is then subjected to a second set of elevated temperature and pressure conditions as discussed above. Typically, the second set of conditions are substantially the same as the first set of conditions. In this way, the second hydrocarbon-containing material can likewise be evaluated for asphaltene precipitation in both upstream and downstream applications, i.e., at reservoir or process conditions, in order to minimize problems associated with asphaltene precipitation in the upstream and downstream applications. The effectiveness of the asphaltene dispersant additives can then be determined as well as optimizing the concentration of the asphaltene dispersant additives in the hydrocarbon-containing material. Typically, the first column is re-used in this step to enhance reproducibility and repeatability of the test. Alternatively, a second column packed with an inert packing material can be used to carry out the evaluation of the second hydrocarbon-containing material sample. In this manner, the evaluation of the first and second hydrocarbon-containing material samples can be conducted in parallel. The second column and inert packing material, if used, are as described above with respect to the first column.

The asphaltenes are then precipitated from the second hydrocarbon-containing material sample with one or more second asphaltene-precipitating mobile phase solvents and captured in the inert packing material in the column. Useful one or more second asphaltene-precipitating mobile phase solvents can be any of those discussed above and can be determined by one skilled in the art. In one embodiment, the asphaltene-precipitating mobile phase solvent is n-heptane. In one embodiment, the asphaltene-precipitating mobile phase solvent is n-heptane. However, other asphaltene-precipitating mobile phase solvents such as, for example, n-pentane or n-hexane may be used.

In one embodiment, the sample solution is passed into the first column or a second column, and then one or more second asphaltene-precipitating mobile phase solvents are passed through the column. The one or more second asphaltene-precipitating mobile phase solvents should be passed into the column for a time period sufficient to elute the soluble fraction, commonly known as maltenes or petrolenes, and induce precipitation of the insoluble fraction, i.e., the precipitated asphaltenes, from the second hydrocarbon-containing material sample. Generally, once the second asphaltene-precipitating mobile phase solvent enters the first column, the second asphaltene-precipitating mobile phase solvent dilutes and displaces the solvent in the sample solution, thereby allowing the asphaltenes to substantially precipitate therefrom. The soluble fraction then elutes from the first column.

In another embodiment, the second hydrocarbon-containing material sample is first combined with one or more second asphaltene-precipitating mobile phase solvents to induce precipitation of the insoluble fraction, i.e., the precipitated asphaltenes, from the hydrocarbon-containing material sample and form a soluble fraction. The solution is then passed into the first column or a second column such that the precipitated asphaltenes are captured in the inert packing material and the soluble fraction is eluted through the column.

Next, the precipitated asphaltenes are dissolved at a predetermined temperature once substantially all of the soluble fraction has eluted. In general, once substantially all of the soluble fraction has eluted the column is allowed to cool to a predetermined temperature. The column can be cooled naturally or through a refrigerant such as nitrogen or liquid carbon dioxide. The precipitated asphaltenes are then dissolved employing one or more second solvents having a solubility parameter of at least about 21 $MPa^{0.5}$ but no greater than about 30 $MPa^{0.5}$. A solubility parameter as described herein is determined by the Hansen's methodology described in Barton, A. F. M. *Handbook of Solubility Parameters and Other Cohesion Parameters*; CRC Pres Inc.: Boca Raton, Fla., p. 95 (1983).

Suitable one or more second solvents having a solubility parameter of at least about 21 $MPa^{0.5}$ but no greater than about 30 $MPa^{0.5}$ can be any of those discussed above with respect to the first solvents solvents having a solubility parameter of at least about 21 $MPa^{0.5}$ but no greater than about 30 $MPa^{0.5}$ and can determined by one skilled in the art. It is also contemplated that blends of such solvents can be used. In one embodiment, a blend can contain from about 0.5 wt. % to about 99.5 wt. % chlorinated solvent and from about 99.5 wt. % to about 0.5 wt. % alcohol solvent. In another embodiment, a blend can contain from about 80 wt. % to about 95 wt. % chlorinated solvent and from about 20 wt. % to about 5 wt. % alcohol solvent.

The asphaltene concentration in the eluted fraction from the column is then determined in the same manner as discussed above with respect to the first sample.

Once the asphaltene concentration of the second sample has been obtained, it is then compared with the asphaltene concentration of the first sample. In this manner, the effectiveness of the asphaltene dispersant additive(s) when used in one or more hydrocarbon-containing material which have been or are being subjected to elevated temperature and pressure conditions can be determined in order to, for example, (1) improve flow of a hydrocarbon-containing feedstock from a well, wellhead or a production line proximate the wellhead or (2) reduce fouling in one or more crude hydrocarbon refinery components located within a refinery.

In accordance with one embodiment of the present invention, there is provided a method for optimizing the concentration of asphaltene dispersant additives in a hydrocarbon-containing material, the method comprising the steps of:

(a) selecting a suitable concentration of asphaltene dispersant additives for adding to a hydrocarbon-containing material, wherein the selection of the concentration of the asphaltene dispersant additives comprises receiving data corresponding to the effectiveness of the concentration of asphaltene dispersant additives for inhibiting or preventing asphaltene precipitation in a hydrocarbon-containing material subjected to elevated temperature and pressure conditions; wherein the data is derived from:

(i) subjecting a first column having an inert packing material therein to a first set of elevated temperature and pressure conditions;

(ii) precipitating an amount of asphaltenes from a first hydrocarbon-containing material sample having solvated asphaltenes therein with one or more first asphaltene-precipitating mobile phase solvents and capturing the precipitated asphaltenes in the inert packing material in the first column;

(iii) dissolving an amount of the precipitated asphaltenes at a predetermined temperature with one or more first solvents having a solubility parameter of at least about 21 $MPa^{0.5}$ but no greater than about 30 $MPa^{0.5}$ to elute a fraction having dissolved asphaltenes therein;

(iv) determining the asphaltene content of the first sample by the concentration of asphaltenes in the eluted fraction from the first column;

(v) subjecting the first column or a second column having an inert packing material therein to a second set of elevated temperature and pressure conditions;

(vi) precipitating an amount of asphaltenes from a second hydrocarbon-containing material sample containing one or more asphaltene dispersant additives and having solvated asphaltenes therein with one or more second asphaltene-precipitating mobile phase solvents and capturing the precipitated asphaltenes in the inert packing material in the second column;

(vii) dissolving an amount of the precipitated asphaltenes at a predetermined temperature with one or more second solvents having a solubility parameter of at least about 21 $MPa^{0.5}$ but no greater than about 30 $MPa^{0.5}$ to elute a fraction having dissolved asphaltenes therein;

(viii) determining the asphaltene content of the second sample by the concentration of asphaltenes in the eluted fraction from the second column; and (ix) comparing the asphaltene content of the first sample with the asphaltene content of the second sample; and (b) injecting the selected concentration of asphaltene dispersant additives into the well, wellhead, a production line proximate the wellhead or a refinery line susceptible to fouling.

The information obtained from the method of the present invention can then be stored in a relational database. For example, a relational database can be electrically connected to a signal data collector comprising a computer microprocessor for system operation and control to collect the data from the various tests over an extended period of time to compile a library therefrom. The database can be used to find optimum combinations for a desired product stream, and can be particularly useful when the desired product stream varies depending on market factors. When the product requirements change, appropriate combinations can be selected to prepare the desired product.

Once the effectiveness of the one or more asphaltene dispersant additives has been determined and/or concentration of the one or more asphaltene dispersant additives has been optimized, one or more asphaltene dispersant additives can be selected based on this data for use in both upstream and downstream applications. In one embodiment, the one or more of the selected asphaltene dispersant additives are injected into the well, wellhead or a production line proximate the wellhead. In this manner, the selected one or more asphaltene dispersant additives can be added in an effective amount to the hydrocarbon-containing material in order to minimize precipitation of the asphaltenes from the hydrocarbon-containing material.

In one embodiment, the selected one or more asphaltene dispersant additives are added to one or more of hydrocarbon-containing feedstock which are then used as a refinery feedstock in one or more crude hydrocarbon refining components within a refinery and subjected to one or more conventional hydroprocessing techniques such as hydrotreating, hydrocracking, hydrogenation, hydrofinishing and hydroisomerization and the like. The refinery hydroprocesses that the one or more of the selected hydrocarbon-containing feedstocks can be used in are well known in the art.

The term "crude hydrocarbon refinery component" generally refers to an apparatus or instrumentality of a process to refine crude hydrocarbons, such as an oil refinery process. Crude hydrocarbon refinery components include, but are not limited to, heat transfer components such as a heat exchanger, a furnace, a crude preheater, a coker preheater, or any other heaters, a FCC slurry bottom, a debutanizer exchanger/tower, other feed/effluent exchangers and furnace air preheaters in refinery facilities, flare compressor components in refinery facilities and steam cracker/reformer tubes in petrochemical facilities. Crude hydrocarbon refinery components can also include other instrumentalities in which heat transfer may take place, such as a fractionation or distillation column, a scrubber, a reactor, a liquid-jacketed tank, a pipestill, a coker and a visbreaker. It is understood that "crude hydrocarbon refinery components," as used herein, encompass tubes, piping, baffles and other process transport mechanisms that are internal to, at least partially constitute, and/or are in direct fluid communication with, any one of the above-mentioned crude hydrocarbon refinery components.

In one embodiment, representative examples of such crude hydrocarbon refinery components include a heat exchanger, a furnace, a crude preheater, a coker preheater, a FCC slurry bottom, a debutanizer exchanger, a debutanizer tower, a feed/effluent exchanger, a furnace air preheater, a flare compressor component, a steam cracker, a steam reformer, a distillation column, a fractionation column, a scrubber, a reactor, a liquid-jacketed tank, a pipestill, a coker, a storage tank, a visbreaker and the like.

Accordingly, another embodiment of the present invention is directed to a method for reducing fouling in one or more crude hydrocarbon refinery components located within a refinery, the method comprising the steps of:
  (a) selecting one or more asphaltene dispersant additives for adding to one or more hydrocarbon-containing feedstocks to be refined, wherein the selection of the one or more asphaltene dispersant additives comprises receiving data corresponding to the effectiveness of the one or more asphaltene dispersant additives for inhibiting or preventing asphaltene precipitation in a hydrocarbon-containing feedstock subjected to elevated temperature and pressure conditions; wherein the data is derived from:
    (i) subjecting a first column having an inert packing material therein to a first set of elevated temperature and pressure conditions;
    (ii) precipitating an amount of asphaltenes from a first hydrocarbon-containing feedstock sample having solvated asphaltenes therein with one or more first asphaltene-precipitating mobile phase solvents and capturing the precipitated asphaltenes in the inert packing material in the first column;
    (iii) dissolving an amount of the precipitated asphaltenes at a predetermined temperature with one or more first solvents having a solubility parameter of at least about 21 $MPa^{0.5}$ but no greater than about 30 $MPa^{0.5}$ to elute a fraction having dissolved asphaltenes therein;
    (iv) determining the asphaltene content of the first sample by the concentration of asphaltenes in the eluted fraction from the first column;
    (v) subjecting the first column or a second column having an inert packing material therein to a second set of elevated temperature and pressure conditions;
    (vi) precipitating an amount of asphaltenes from a second hydrocarbon-containing feedstock sample containing one or more asphaltene dispersant additives and having solvated asphaltenes therein with one or more second asphaltene-precipitating mobile phase solvents and capturing the precipitated asphaltenes in the inert packing material in the second column;
    (vii) dissolving an amount of the precipitated asphaltenes at a predetermined temperature with one or more second solvents having a solubility parameter of at least about 21 $MPa^{0.5}$ but no greater than about 30 $MPa^{0.5}$ to elute a fraction having dissolved asphaltenes therein;
    (viii) determining the asphaltene content of the second sample by the concentration of asphaltenes in the eluted fraction from the second column; and
    (ix) comparing the asphaltene content of the first sample with the asphaltene content of the second sample;
  (b) adding an effective amount of the selected one or more asphaltene dispersant additives to the one or more hydrocarbon-containing feedstocks to be refined; and
  (c) feeding the one or more hydrocarbon-containing feedstocks to the one or more crude hydrocarbon refinery components.

In accordance with another embodiment of the present invention, there is provided a system capable of experiencing fouling conditions associated with particulate or asphaltene fouling, the system comprising:
  (a) one or more crude hydrocarbon refinery components; and
  (b) one or more hydrocarbon-containing feedstocks containing one or more asphaltene dispersant additives therein for providing a hydrocarbon-containing feedstock having a stable plurality of asphaltene components, wherein the one or more hydrocarbon-containing feedstocks are in fluid communication with the one or more crude hydrocarbon refinery components, and further wherein selection of the one or more asphaltene dispersant additives comprises receiving data corresponding to the effectiveness of the one or more asphaltene dispersant additives for inhibiting or preventing asphaltene precipitation in a hydrocarbon-containing feedstock subjected to elevated temperature and pressure conditions; wherein the data is derived from:
    (i) subjecting a first column having an inert packing material therein to a first set of elevated temperature and pressure conditions;
    (ii) precipitating an amount of asphaltenes from a first hydrocarbon-containing feedstock sample having solvated asphaltenes therein with one or more first asphaltene-precipitating mobile phase solvents and capturing the precipitated asphaltenes in the inert packing material in the first column;
    (iii) dissolving an amount of the precipitated asphaltenes at a predetermined temperature with one or more first solvents having a solubility parameter of at least about 21 $MPa^{0.5}$ but no greater than about 30 $MPa^{0.5}$ to elute a fraction having dissolved asphaltenes therein;
    (iv) determining the asphaltene content of the first sample by the concentration of asphaltenes in the eluted fraction from the first column;

(v) subjecting the first column or a second column having an inert packing material therein to a second set of elevated temperature and pressure conditions;
(vi) precipitating an amount of asphaltenes from a second hydrocarbon-containing feedstock sample containing one or more asphaltene dispersant additives and having solvated asphaltenes therein with one or more second asphaltene-precipitating mobile phase solvents and capturing the precipitated asphaltenes in the inert packing material in the second column;
(vii) dissolving an amount of the precipitated asphaltenes at a predetermined temperature with one or more second solvents having a solubility parameter of at least about 21 $MPa^{0.5}$ but no greater than about 30 $MPa^{0.5}$ to elute a fraction having dissolved asphaltenes therein;
(viii) determining the asphaltene content of the second sample by the concentration of asphaltenes in the eluted fraction from the second column; and
(ix) comparing the asphaltene content of the first sample with the asphaltene content of the second sample.

The following non-limiting examples are illustrative of the present invention.

EXAMPLE 1

Two solutions of a heavy crude oil vacuum residue from Mexico (API (60/60)=1, and 96% wt. of 1000° F.) with and without an asphaltene dispersant additive (200 ppm of nonylphenol formaldehyde with a mol. weight of 1800 g/mol), were prepared by dissolving 0.1000 g of the heavy crude oil in 10 mL of methylene chloride. A stainless steel column packed with poly(tetrafluoroethylene) (PTFE) were placed in a Polaratherm™ Series 9000 liquid chromatograph oven commercially available from Selerity Technologies (Salt Lake City, Utah), and heated to 195° C. and pressurized to 580 psi (40 bar). The solution without an asphaltene dispersant additive was then injected into the stainless steel column using a heptane mobile phase at a flow rate of 2 mL/min. The maltenes (heptane solubles) eluted from the column as the first peak around 2 minutes after the injection while precipitated asphaltenes at this temperature remained inside the column in the PTFE.

Next, the oven was cooled down to 35° C. and when it reaches that temperature the mobile phase was switched to 10% methanol/90% dichloromethane (Solubility Parameter of 21.23 MPa0.5), to redissolve the asphaltenes retained in the column (peak around 15 min). Once they were eluted, the temperature was increased to 110° C. to clean the column of any adsorbed species (peak around 30 min) and the solvent was switched back to 100% n-heptane for the next run.

This procedure was then carried out as discussed above except the solution without an asphaltene dispersant additive was replaced with the solution containing asphaltene dispersant additive.

The eluted fractions of each solution were quantified using a charge aerosol detector (CAD) operating at the following conditions: nebulizer at 35° C., nitrogen pressure at 35 psi, ion trap volt 20.5V and Corona Volt of 2.41 kV. In this detector, the particles charge was measured by a highly sensitive electrometer. This generates a signal in direct proportion to the quantity of sample present.

FIG. 1 shows the resulting LC-Trace of the asphaltenes as response versus time using the CAD. This figure indicates the presence of three distinct features represented by separated peaks. In FIG. 1, the first peak corresponds to the eluted maltenes (heptane solubles), the second peak corresponds to the eluted asphaltenes and the third signal corresponds to the adsorbed species. As can be seen, the asphaltene peak was smaller in the presence of additives indicating the effect of the asphaltene dispersant additive in maintaining the asphaltenes in solution.

Additionally, the CAD allows for calculating the peak area for each separated peaks which is directly proportional to the content for each eluted fraction. By injecting different amounts of asphaltenes and maltenes, the proportionality constants (also known as response factors) can be determined for these two materials. Then, maltenes and asphaltenes contents (in mg) can be calculated by simply multiplying the peak area of an unknown sample by the corresponding response factor. This technique is commonly used in HPLC and other chromatographic separations. The mass balances can be determined to demonstrate the validity of the data. These results are shown in Table 1 below.

TABLE 1

| Sample | Maltene Content (mg) | Asphaltene Content (mg) | Adsorbed Material (mg) | Mass Balance | % Red. Asphaltenes[1] |
|---|---|---|---|---|---|
| Mexican VR | 23.50 | 10.25 | 1.20 | 95% | — |
| Mexican VR + 200 ppm NPF-1800 | 28.94 | 6.12 | 0.44 | 96 | −40% |

[1]Percentage of reduction of asphaltene content with respect to the case without asphaltene dispersant additive In Table 1, the percentage of reduction of asphaltene is calculated by the following equation (1):

% Reduction of Asphaltenes=100×(Asphaltene Content with additives−Asphaltene Content without additives)/(Asphaltene Content without additives)   (1)

The percentage of reduction of asphaltenes is used to measure the effectiveness of an asphaltene dispersant additive. The more negative this value is, the more effective is the additive for keeping the asphaltenes dissolved in the hydrocarbon containing feedstock at any given temperature or pressure.

EXAMPLE 2

Figure 2:
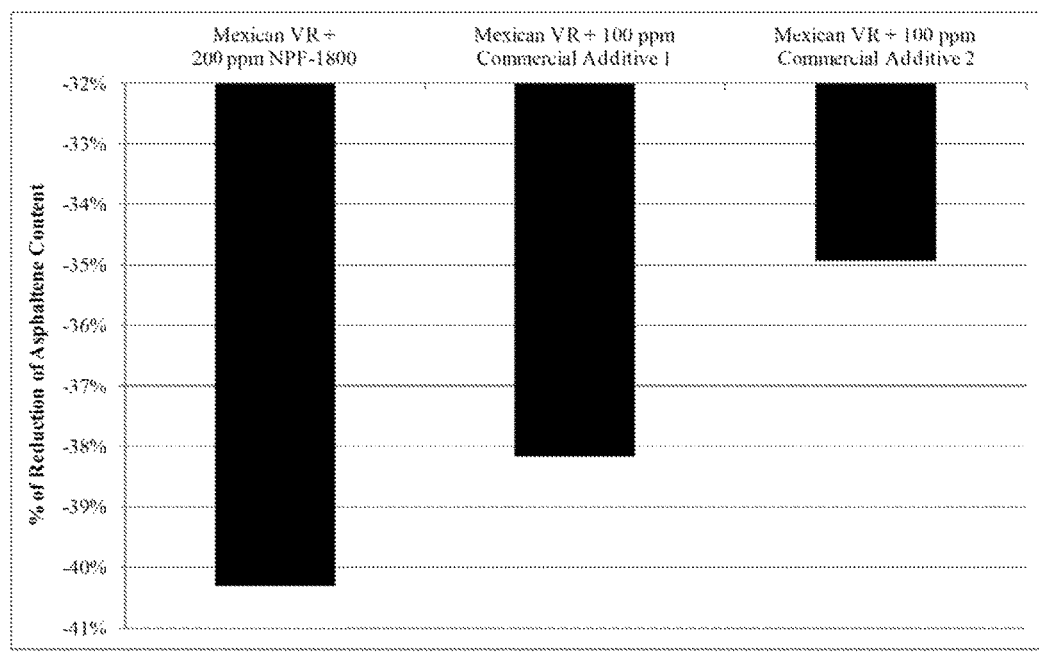
FIG. 2 is a graph showing the percentage of reduction of asphaltene content for a Mexican vacuum residue (1000+° F.) using different asphaltene dispersant additives at 195° C.

Determining the Effectiveness of Asphaltene Dispersant Additives in a Mexican Vacuum Residue In FIG. 2, the percentages of reduction of asphaltene contents with respect to the case without asphaltene dispersant additive are presented for nonylphenol formaldehyde and two commercial asphaltene dispersant additives at 195° C. As can be seen, this method can be used to determining the effectiveness of one or more asphaltene dispersant additives for inhibiting or preventing asphaltene precipitation of a vacuum residue.

EXAMPLE 3

Figure 3:
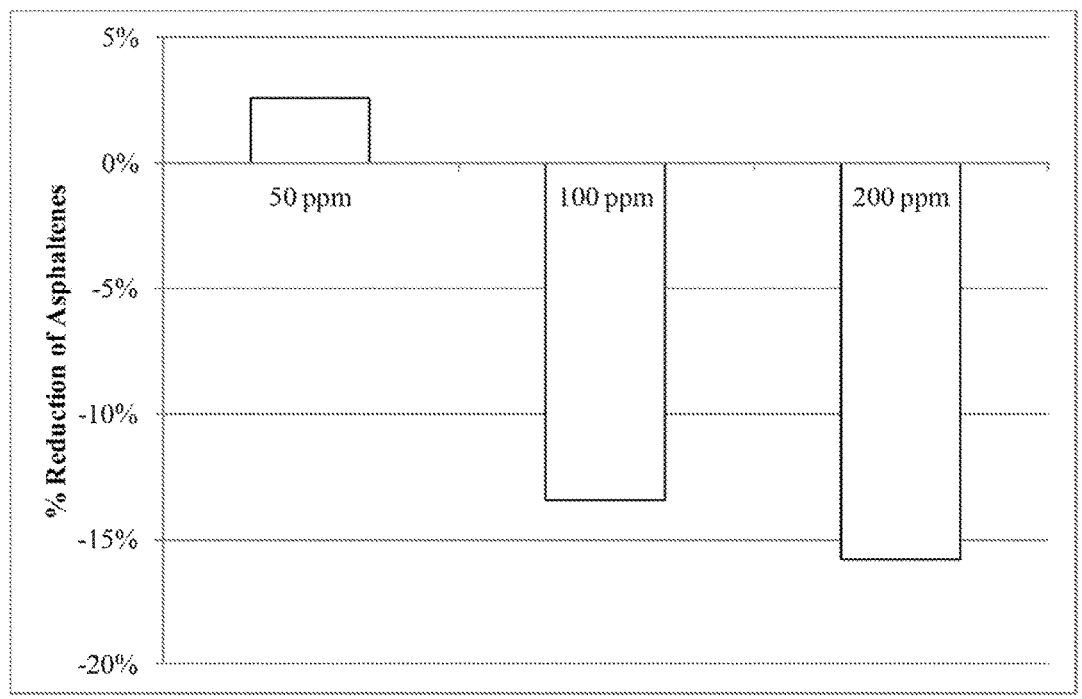
FIG. 3 is a graph showing the percentage of reduction of asphaltene content for a Venezuelan vacuum residue (1000+° F.) using different concentrations of asphaltene dispersant additives at 195° C.

Determining the Optimum Concentration of an Asphaltene Dispersant Additives a Venezuelan Vacuum Residue In FIG. 3, the percentages of reduction of asphaltene contents with respect to the case without asphaltene dispersant additive are presented for a Venezuelan vacuum residue (API (60/60)=2.7, and 98% wt. of $1000^{+\circ}$ F.) at 195° C.

using a commercial asphaltene dispersant additive 3. As can be seen, this method can be used to determining the optimum concentration of a asphaltene dispersant additives for inhibiting or preventing asphaltene precipitation of a vacuum residue.

EXAMPLE 4

Figure 4:
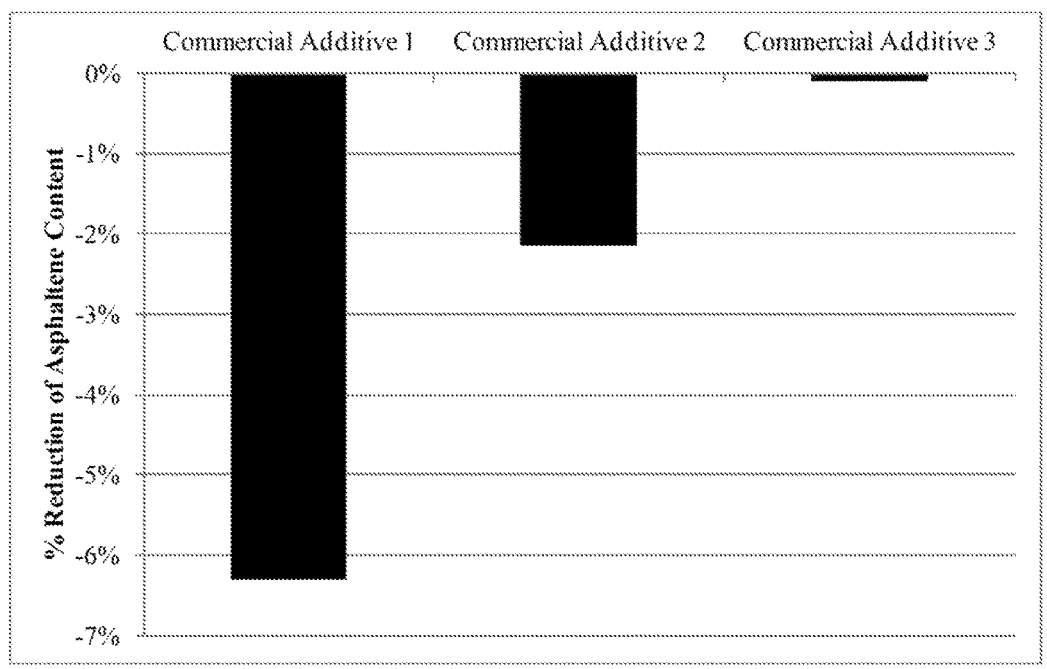
FIG. 4 is a graph showing the percentage of reduction of asphaltene content for a Mid North America crude oil using different commercial asphaltene dispersant additives at 35° C.

Determining the Effectiveness of Asphaltene Dispersant Additives in Mid North America Crude Oil In FIG. 4, the percentages of reduction of asphaltene contents with respect to the case without asphaltene dispersant additive are presented for a Mid North America crude oil with asphaltene precipitation problems. These runs were carried out using 100 ppm of the commercial asphaltene dispersant additives 1-3 at 35° C. and 600 psi. As can be seen, this method can be used to determining the effectiveness of one or more asphaltene dispersant additives for inhibiting or preventing asphaltene precipitation of a crude oil with asphaltene precipitation problems.

EXAMPLE 5

Figure 5:
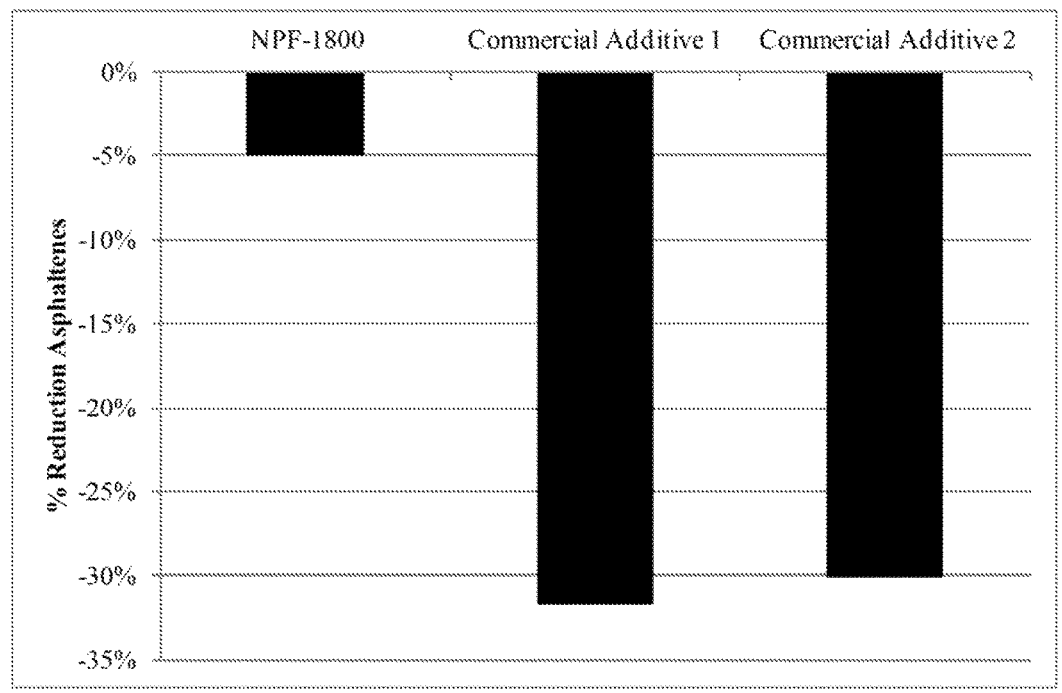
FIG. 5 is a graph showing the percentage of reduction of asphaltene content for a hydroprocessed product using different commercial asphaltene dispersant additives at 150° C.

Determining the Effectiveness of Asphaltene Dispersant Additives in a Hydroprocessed Product In FIG. 5, the percentages of reduction of asphaltene content with respect to the case without asphaltene dispersant additive are presented for a hydroprocessed product with fouling tendencies. These runs were carried out using 100 ppm of the commercial asphaltene dispersant additives 1 and 2 at 150° C. As can be seen this method can be used to determining the effectiveness of one or more asphaltene dispersant additives for inhibiting or preventing asphaltene precipitation of a hydroprocessed product with high tendency of fouling heat exchangers.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the claims appended hereto.

What is claimed is:

1. A method for determining an effectiveness of one or more asphaltene dispersant additives for inhibiting or preventing asphaltene precipitation in a hydrocarbon-containing material subjected to an elevated temperature and pressure conditions, the method comprising the steps of:
   (a) subjecting a first column having an inert packing material therein to a first set of the elevated temperature and pressure conditions comprising a temperature ranging from 140° C. to 450° C. and a pressure ranging from 1 to 200 standard atmosphere (atm);
   (b) precipitating an amount of asphaltenes from a first hydrocarbon-containing material sample having solvated asphaltenes therein with one or more first asphaltene-precipitating mobile phase solvents and capturing precipitated asphaltenes in the inert packing material in the first column;
   (c) dissolving an amount of the precipitated asphaltenes at a predetermined temperature with one or more first solvents having a solubility parameter of at least 21 $MPa^{0.5}$ but no greater than 30 $MPa^{0.5}$ to elute a first fraction having dissolved asphaltenes therein;
   (d) determining an asphaltene content of the first hydrocarbon-containing material sample by a concentration of asphaltenes in an eluted fraction from the first column;
   (e) subjecting the first column or a second column having the inert packing material therein to a second set of the elevated temperature and pressure conditions, wherein the second set of the elevated temperature and pressure conditions are substantially the same conditions as the first set of the elevated temperature and pressure conditions and comprise the temperature ranging from 140° C. to 450° C. and the pressure ranging from 1 to 200 atm;
   (f) precipitating an amount of asphaltenes from a second hydrocarbon-containing material sample containing one or more asphaltene dispersant additives and having solvated asphaltenes therein with one or more second asphaltene-precipitating mobile phase solvents and capturing the precipitated asphaltenes in the inert packing material in the second column;
   (g) dissolving an amount of the precipitated asphaltenes at the predetermined temperature with one or more second solvents having the solubility parameter of at least 21 $MPa^{0.5}$ but no greater than 30 $MPa^{0.5}$ to elute a second eluted fraction having dissolved asphaltenes therein;
   (h) determining the asphaltene content of the second hydrocarbon-containing material sample by the concentration of asphaltenes in the second eluted fraction from the first column or the second column; and
   (i) comparing the asphaltene content of the first hydrocarbon-containing material sample with the asphaltene content of the second hydrocarbon-containing material sample to determine the effectiveness of one or more asphaltene dispersant additives for inhibiting or preventing asphaltene precipitation in the hydrocarbon-containing material subjected to the elevated temperature and pressure conditions.

2. The method of claim 1, wherein the first hydrocarbon-containing material sample and the second hydrocarbon-containing material sample are the same and comprise coal tars, shale oils, shale, tar sand bitumen, asphalts, light crude oil, and heavy crude oil or fractions thereof.

3. The method of claim 1, wherein the one or more first solvents and the one or more second solvents having the solubility parameter of at least 21 $MPa^{0.5}$ but no greater than 30 $MPa^{0.5}$ comprise a blend containing from 0.5 wt. % to 99.5 wt. % of one or more chlorinated solvents and from 99.5 wt. % to 0.5 wt. % of one or more alcohol solvents.

4. The method of claim 1, wherein the asphaltene content of the eluted fraction of the first hydrocarbon-containing material sample and the second hydrocarbon-containing material sample is determined by a high-performance liquid chromatograph (HPLC).

5. The method of claim 1, wherein an amount of the one or more asphaltene dispersant additives added to the second hydrocarbon-containing material sample is from 0.1 to 50,000 mg of asphaltene dispersant additive per kilogram of the second hydrocarbon-containing material sample.

6. The method of claim 1, further comprising a step of storing results of comparing of step (i) in a database.

7. A method for reducing fouling in one or more crude hydrocarbon refinery components located within a refinery, the method comprising the steps of:
   (a) selecting one or more asphaltene dispersant additives for adding to one or more hydrocarbon-containing feedstocks to be refined, wherein a selection of the one or more asphaltene dispersant additives comprises receiving data corresponding to an effectiveness of the one or more asphaltene dispersant additives for inhibiting or preventing asphaltene precipitation in a hydrocarbon-containing material subjected to elevated temperature and pressure conditions; wherein the data is derived from:
      (i) subjecting a first column having an inert packing material therein to a first set of the elevated temperature and pressure conditions comprising a temperature ranging from 140° C. to 450° C. and a pressure ranging from 1 to 200 atm;
      (ii) precipitating an amount of asphaltenes from a first hydrocarbon-containing material sample having solvated asphaltenes therein with one or more first asphaltene-precipitating mobile phase solvents and capturing precipitated asphaltenes in the inert packing material in the first column;
      (iii) dissolving an amount of the precipitated asphaltenes at a predetermined temperature with one or more first solvents having a solubility parameter of at least 21 $MPa^{0.5}$ but no greater than 30 $MPa^{0.5}$ to elute a first fraction having dissolved asphaltenes therein;
      (iv) determining an asphaltene content of the first hydrocarbon-containing material sample by a concentration of asphaltenes in an eluted fraction from the first column;
      (v) subjecting the first column or a second column having the inert packing material therein to a second set of elevated temperature and pressure conditions, wherein the second set of the elevated temperature and pressure conditions are substantially the same conditions as first set of the elevated temperature and pressure conditions and comprise a temperature ranging from 140° C. to 450° C. and a pressure ranging from 1 to 200 atm;
      (vi) precipitating an amount of asphaltenes from a second hydrocarbon-containing material sample containing the one or more asphaltene dispersant additives and having solvated asphaltenes therein with one or more second asphaltene-precipitating mobile phase solvents and capturing the precipitated asphaltenes in the inert packing material in the second column;
      (vii) dissolving an amount of the precipitated asphaltenes at the predetermined temperature with one or more second solvents having the solubility parameter of at least 21 $MPa^{0.5}$ but no greater than 30 $MPa^{0.5}$ to elute a second eluted fraction having dissolved asphaltenes therein;
      (viii) determining the asphaltene content of the second hydrocarbon-containing material sample by the concentration of asphaltenes in the second eluted fraction from the first column or the second column; and
      (ix) comparing the asphaltene content of the first hydrocarbon-containing material sample with the asphaltene content of the second hydrocarbon-containing material sample;
   (b) adding one or more of selected asphaltene dispersant additives from step (a) to the one or more hydrocarbon-containing feedstocks to be refined; and
   (c) feeding the one or more hydrocarbon-containing feedstocks to the one or more crude hydrocarbon refinery components.

8. The method of claim 7, wherein an amount of the one or more asphaltene dispersant additives added to the second hydrocarbon-containing material sample is from 0.1 to 50,000 mg of asphaltene dispersant additive per kilogram of the second hydrocarbon-containing material sample.

9. The method of claim 7, wherein the one or more crude hydrocarbon refinery components are selected from the group consisting of a heat exchanger, a furnace, a crude preheater, a coker preheater, a FCC slurry bottom, a debutanizer exchanger, a debutanizer tower, a feed/effluent exchanger, a furnace air preheater, a flare compressor component, a steam cracker, a steam reformer, a distillation column, a fractionation column, a scrubber, a reactor, a liquid-jacketed tank, a pipestill, a coker, a storage tank and a visbreaker.

10. A system capable of experiencing fouling conditions associated with particulate or asphaltene fouling, the system comprising:
   (a) one or more crude hydrocarbon refinery components; and
   (b) one or more hydrocarbon-containing feedstocks containing one or more asphaltene dispersant additives therein for providing a hydrocarbon-containing feedstock having a stable plurality of asphaltene components, wherein the one or more hydrocarbon-containing feedstocks are in fluid communication with the one or more crude hydrocarbon refinery components, and further wherein a selection of the one or more asphaltene dispersant additives comprises receiving data corresponding to an effectiveness of the one or more asphaltene dispersant additives for inhibiting or preventing asphaltene precipitation in a hydrocarbon-containing feedstock subjected to an elevated temperature and pressure conditions; wherein the data is derived from:
      (i) subjecting a first column having an inert packing material therein to a first set of the elevated temperature and pressure conditions comprising a temperature ranging from 140° C. to 450° C. and a pressure ranging from 1 to 200 atm;
      (ii) precipitating an amount of asphaltenes from a first hydrocarbon-containing feedstock sample having solvated asphaltenes therein with one or more first asphaltene-precipitating mobile phase solvents and capturing precipitated asphaltenes in the inert packing material in the first column;
   (iii) dissolving an amount of the precipitated asphaltenes at a predetermined temperature with one or more first solvents having a solubility parameter of at least 21 $MPa^{0.5}$ but no greater than 30 $MPa^{0.5}$ to elute a first fraction having dissolved asphaltenes therein;
      (iv) determining an asphaltene content of the first hydrocarbon-containing feedstock sample by a concentration of asphaltenes in an eluted fraction from the first column;
      (v) subjecting the first column or a second column having the inert packing material therein to a second set of elevated temperature and pressure conditions, wherein the second set of the elevated temperature and pressure conditions are substantially the same conditions as the first set of the elevated temperature and pressure conditions and comprise the temperature ranging from 140° C. to 450° C. and the pressure ranging from 1 to 200 atm;

(vi) precipitating an amount of asphaltenes from a second hydrocarbon-containing feedstock sample containing the one or more asphaltene dispersant additives and having solvated asphaltenes therein with one or more second asphaltene-precipitating mobile phase solvents and capturing the precipitated asphaltenes in the inert packing material in the second column;

(vii) dissolving an amount of the precipitated asphaltenes at the predetermined temperature with one or more second solvents having the solubility parameter of at least 21 $MPa^{0.5}$ but no greater than 30 $MPa^{0.5}$ to elute a second eluted fraction having dissolved asphaltenes therein;

(viii) determining the asphaltene content of the second hydrocarbon-containing feedstock sample by the concentration of asphaltenes in the second eluted fraction from the first column or the second column; and (ix) comparing the asphaltene content of the first hydrocarbon-containing feedstock sample with the asphaltene content of the second hydrocarbon-containing feedstock sample.

11. The system of claim 10, wherein an amount of the one or more asphaltene dispersant additives added to the second hydrocarbon-containing feedstock sample is from 0.1 to 50000 mg of asphaltene dispersant additive per kilogram of the second hydrocarbon-containing feedstock sample.

12. The system of claim 10, wherein the one or more crude hydrocarbon refinery components are selected from the group consisting of a heat exchanger, a furnace, a crude preheater, a coker preheater, a FCC slurry bottom, a debutanizer exchanger, a debutanizer tower, a feed/effluent exchanger, a furnace air preheater, a flare compressor component, a steam cracker, a steam reformer, a distillation column, a fractionation column, a scrubber, a reactor, a liquid-jacketed tank, a pipestill, a coker, a storage tank and a visbreaker.

13. A method comprising the steps of:

(a) selecting one or more asphaltene dispersant additives for adding to a hydrocarbon-containing feedstock, wherein a selection of the one or more asphaltene dispersant additives comprises receiving data corresponding to an effectiveness of the one or more asphaltene dispersant additives for inhibiting or preventing asphaltene precipitation in a hydrocarbon-containing feedstock subjected to an elevated temperature and pressure conditions; wherein the data is derived from:

(i) subjecting a first column having an inert packing material therein to a first set of the elevated temperature and pressure conditions comprising a temperature ranging from 140° C. to 450° C. and a pressure ranging from 1 to 200 atm;

(ii) precipitating an amount of asphaltenes from a first hydrocarbon-containing feedstock sample having solvated asphaltenes therein with one or more first asphaltene-precipitating mobile phase solvents and capturing precipitated asphaltenes in the inert packing material in the first column;

(iii) dissolving an amount of the precipitated asphaltenes at a predetermined temperature with one or more first solvents having a solubility parameter of at least 21 $MPa^{0.5}$ but no greater than 30 $MPa^{0.5}$ to elute a first fraction having dissolved asphaltenes therein;

(iv) determining an asphaltene content of the first hydrocarbon-containing feedstock sample by a concentration of asphaltenes in an eluted fraction from the first column;

(v) subjecting the first column or a second column having the inert packing material therein to a second set of elevated temperature and pressure conditions, wherein the second set of the elevated temperature and pressure conditions are substantially the same conditions as the first set of the elevated temperature and pressure conditions and comprise the temperature ranging from 140° C. to 450° C. and the pressure ranging from 1 to 200 atm;

(vi) precipitating an amount of asphaltenes from a second hydrocarbon-containing feedstock sample containing the one or more asphaltene dispersant additives and having solvated asphaltenes therein with one or more second asphaltene-precipitating mobile phase solvents and capturing the precipitated asphaltenes in the inert packing material in the second column;

(vii) dissolving an amount of the precipitated asphaltenes at the predetermined temperature with one or more second solvents having the solubility parameter of at least 21 $MPa^{0.5}$ but no greater than 30 $MPa^{0.5}$ to elute a second eluted fraction having dissolved asphaltenes therein;

(viii) determining the asphaltene content of the second hydrocarbon-containing feedstock sample by the concentration of asphaltenes in the second eluted fraction from the first column or the second column; and (ix) comparing the asphaltene content of the first hydrocarbon-containing feedstock sample with the asphaltene content of the second hydrocarbon-containing feedstock sample; and (b) injecting one or more selected asphaltene dispersant additives into a well, a wellhead or a production line proximate the wellhead.

14. The method of claim 13, wherein an amount of the one or more asphaltene dispersant additives added to the second hydrocarbon-containing feedstock sample is from 0.1 to 50000 mg of asphaltene dispersant additive per kilogram of the second hydrocarbon-containing feedstock sample.

15. A method comprising the steps of:

(a) selecting a concentration of one or more asphaltene dispersant additives for adding to a hydrocarbon-containing feedstock, wherein a selection of the concentration of the one or more asphaltene dispersant additives comprises receiving data corresponding to an effectiveness of the concentration of the one or more asphaltene dispersant additives for inhibiting or preventing asphaltene precipitation in a hydrocarbon-containing feedstock subjected to an elevated temperature and pressure conditions; wherein the data is derived from:

(i) subjecting a first column having an inert packing material therein to a first set of the elevated temperature and pressure conditions comprising a temperature ranging from 140° C. to 450° C. and a pressure ranging from 1 to 200 atm;

(ii) precipitating an amount of asphaltenes from a first hydrocarbon-containing feedstock sample having solvated asphaltenes therein with one or more first asphaltene-precipitating mobile phase solvents and capturing precipitated asphaltenes in the inert packing material in the first column;

(iii) dissolving an amount of the precipitated asphaltenes at a predetermined temperature with one or more first solvents having a solubility parameter of at least 21 MPa$^{0.5}$ but no greater than 30 MPa$^{0.5}$ to elute a first fraction having dissolved asphaltenes therein;

(iv) determining an asphaltene content of the first hydrocarbon-containing feedstock sample by a concentration of asphaltenes in an eluted fraction from the first column;

(v) subjecting the first column or a second column having the inert packing material therein to a second set of elevated temperature and pressure conditions, wherein the second set of the elevated temperature and pressure conditions are substantially the same conditions as the first set of the elevated temperature and pressure conditions and comprise the temperature ranging from 140° C. to 450° C. and the pressure ranging from 1 to 200 atm;

(vi) precipitating an amount of asphaltenes from a second hydrocarbon-containing feedstock sample containing one or more asphaltene dispersant additives and having solvated asphaltenes therein with one or more second asphaltene-precipitating mobile phase solvents and capturing the precipitated asphaltenes in the inert packing material in the second column;

(vii) dissolving an amount of the precipitated asphaltenes at the predetermined temperature with one or more second solvents having the solubility parameter of at least 21 MPa$^{0.5}$ but no greater than 30 MPa$^{0.5}$ to elute a second eluted fraction having dissolved asphaltenes therein;

(viii) determining the asphaltene content of the second hydrocarbon-containing feedstock sample by the concentration of asphaltenes in the second eluted fraction from the first column or the second column; and (ix) comparing the asphaltene content of the first hydrocarbon-containing feedstock sample with the asphaltene content of the second hydrocarbon-containing feedstock sample; and (b) injecting the selection of the concentration of the one or more asphaltene dispersant additives into a well, a wellhead, a production line proximate the wellhead or a refinery line susceptible to fouling.

* * * * *